(12) United States Patent
Fisher et al.

(10) Patent No.: US 9,962,375 B2
(45) Date of Patent: May 8, 2018

(54) METHYL-PIPERIDINE COMPOUNDS USEFUL FOR INHIBITING MICROSOMAL PROSTAGLANDIN $E_2$ SYNTHASE-1

(71) Applicant: Eli Lilly and Company, Indianapolis, IN (US)

(72) Inventors: Matthew Joseph Fisher, Mooresville, IN (US); Steven Lee Kuklish, Fishers, IN (US); Peter Rudolph Manninen, Brownsburg, IN (US); Katherine Marie Partridge, Indianapolis, IN (US); Matthew Allen Schiffler, Indianapolis, IN (US); Alan M. Warshawsky, Carmel, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days. days.

(21) Appl. No.: 15/520,462

(22) PCT Filed: Oct. 22, 2015

(86) PCT No.: PCT/US2015/056960
§ 371 (c)(1),
(2) Date: Apr. 20, 2017

(87) PCT Pub. No.: WO2016/069376
PCT Pub. Date: May 6, 2016

(65) Prior Publication Data
US 2017/0326128 A1 Nov. 16, 2017

Related U.S. Application Data

(60) Provisional application No. 62/072,196, filed on Oct. 29, 2014.

(51) Int. Cl.
| | | |
|---|---|---|
| *A61K 31/451* | (2006.01) | |
| *A61K 31/4709* | (2006.01) | |
| *A61K 31/506* | (2006.01) | |
| *C07D 401/04* | (2006.01) | |
| *C07D 405/14* | (2006.01) | |
| *C07D 211/62* | (2006.01) | |
| *A61K 31/00* | (2006.01) | |
| *C07D 211/00* | (2006.01) | |

(52) U.S. Cl.
CPC ........ *A61K 31/451* (2013.01); *A61K 31/4709* (2013.01); *A61K 31/506* (2013.01); *C07D 211/62* (2013.01); *C07D 401/04* (2013.01); *C07D 405/14* (2013.01); *A61K 31/00* (2013.01); *C07D 211/00* (2013.01)

(58) Field of Classification Search
CPC .............. A61K 31/451; A61K 31/4709; A61K 31/506; C07D 401/04; C07D 405/14; C07D 211/62

USPC ........ 546/245, 246, 208, 210; 514/330, 331, 514/326, 317
See application file for complete search history.

(56) References Cited

U.S. PATENT DOCUMENTS

| | | | | |
|---|---|---|---|---|
| 2002/0058900 A1* | 5/2002 | Barbut | ............... | A61M 1/3653 604/8 |
| 2006/0128755 A1* | 6/2006 | Nakagawa | ............ | C07C 237/04 514/332 |
| 2010/0256188 A1* | 10/2010 | Pfau | ..................... | C07D 235/30 514/322 |
| 2010/0324186 A1* | 12/2010 | Birmingham | ............ | C08K 9/02 524/262 |
| 2011/0263556 A1* | 10/2011 | Priepke | ................. | C07C 237/42 514/210.01 |
| 2016/0122330 A1* | 5/2016 | Wannberg | .......... | A61K 31/4545 514/318 |

FOREIGN PATENT DOCUMENTS

| | | |
|---|---|---|
| WO | WO2013146970 A1 | 10/2013 |
| WO | WO2016069374 A1 | 5/2016 |

OTHER PUBLICATIONS

Kablaoui Natasha et al. "Novel Benzoxazole Inhibitors of mPGES-1" Biorganic and Medical Chemistry Letters, (2012) vol. 23, p. 907-911.
Bahia et al. "Inhibitors of Microsomal Prostaglandin E2 Synthase-1 Enzyme as Emerging Anti-Inflammatory Candidates", Medicinal Research Reviews (2014), vol. 34(4), p. 825-855.
Shan He et al., Journal of Medicinal Chemistry, (2013) vol. 56, p. 3296-3309.
Iyer, J.P., et al., Expert Opinion on Therapeutic Targets (2009), vol. 13(7), p. 849-865.

\* cited by examiner

*Primary Examiner* — Matthew P Coughlin
*Assistant Examiner* — Sagar Patel
(74) *Attorney, Agent, or Firm* — Dan I. Wood; James B. Myers

(57) ABSTRACT

The present invention provides compounds of Formula (1), or a pharmaceutically acceptable salt thereof, formula (1), where R, R1, and G are as described herein; methods of preparing the compounds; and use of the compounds to treat pain and/or inflammation associated with arthritis or osteoarthritis.

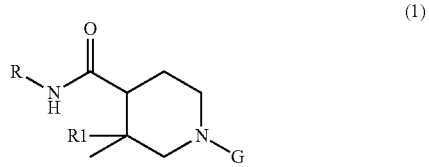

19 Claims, No Drawings

METHYL-PIPERIDINE COMPOUNDS USEFUL FOR INHIBITING MICROSOMAL PROSTAGLANDIN E₂ SYNTHASE-1

The present invention relates to novel compounds; to pharmaceutical compositions comprising the compounds; methods of using the compounds to treat pain and/or inflammation associated with arthritis; and intermediates and processes useful in the synthesis of the compounds.

Arthritis involves inflammation of the joints and is often accompanied by pain and stiffness. Osteoarthritis, the most common form of arthritis, is a complex degenerative disease of the joints characterized by progressive destruction of articular cartilage; peri-articular structures including bones, synovium, and associated fibrous joint tissues; and varying degrees of inflammation. Existing drug therapies using non-steroidal, anti-inflammatory drugs (NSAIDs) and cyclooxygenase-2 inhibitors (COX-2 inhibitors) can reduce pain associated with osteoarthritis, but may be only moderately effective over time and each has variable risk/benefit considerations.

The NSAIDs and COX-2 inhibitors reduce inflammation and pain through inhibition of the COX-2 enzymes. In response to pro-inflammatory stimuli, the COX-2 enzymes metabolize arachidonic acid to prostaglandin H₂ (PGH₂). PGH₂ is further metabolized by a variety of enzymes to other eicosanoids including prostaglandin E₂ (PGE₂), prostaglandin I₂ (PGI₂), prostaglandin F$_{2\alpha}$ (PGF$_{2\alpha}$), prostaglandin D₂ (PGD₂), and thromboxane A₂ (TXA₂). These metabolites are known to induce physiological and pathophysiological effects. It is thought that a drug-mediated imbalance of PGI₂ and TXA₂ may explain why NSAIDs and COX-2 inhibitors produce deleterious gastrointestinal and cardiovascular side-effects. Consequently, these classes of drugs may be contraindicated for many patients due to pre-existing or emergent cardiovascular and/or gastrointestinal conditions. Additionally, patients can become refractory over time to specific drug treatments.

Of the arachidonic acid metabolites, PGE₂ has been identified as an important mediator of conditions associated with osteoarthritis; for example, fever, pain, and inflammation. Prostaglandin E₂ is specifically produced through the metabolism of PGH₂ by microsomal prostaglandin E₂ synthase-1 (mPGES-1). It is thought that selectively inhibiting mPGES-1 may provide a new treatment option for patients suffering from arthritis.

Publication WO 2013/146970 discloses tri-substituted quinoline compounds and suggests that the disclosed compounds may be useful for treating inflammatory diseases inter alia. However, that publication does not disclose compounds as claimed in this application.

There remains a need for additional options to treat the inflammation and alleviate the pain associate with arthritis. The present invention provides novel compounds that inhibit mPGES-1 and that may be beneficial for treating patients suffering from arthritis and osteoarthritis.

The present invention provides compounds according to Formula 1, or pharmaceutically acceptable salts thereof,

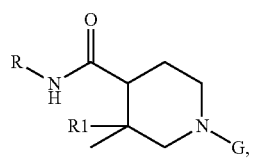

where R1 is H or —CH₃; R is selected from:

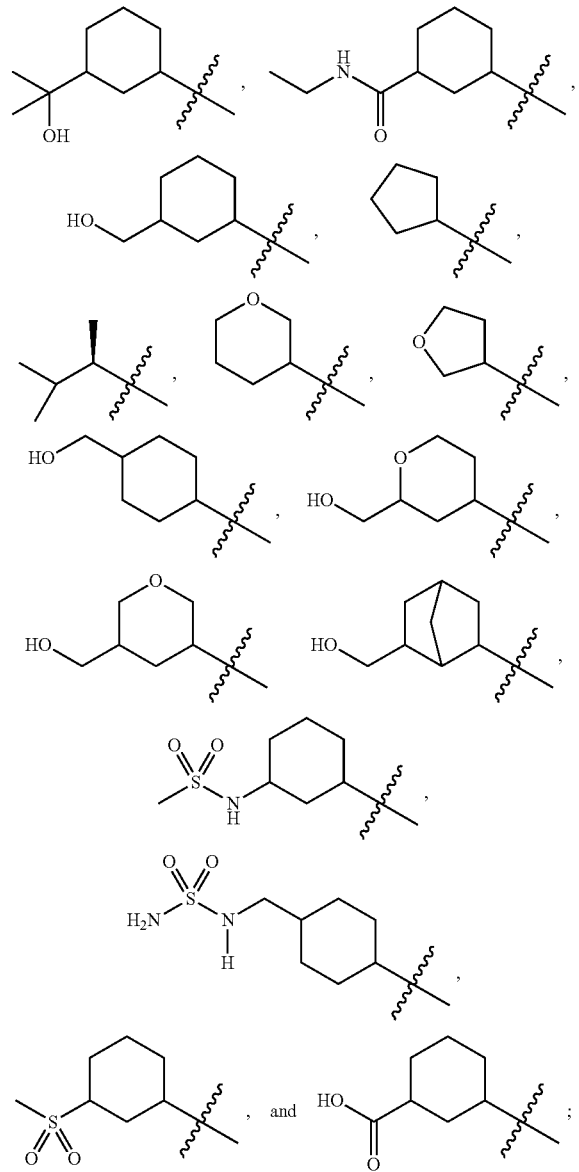

and

G is selected from:

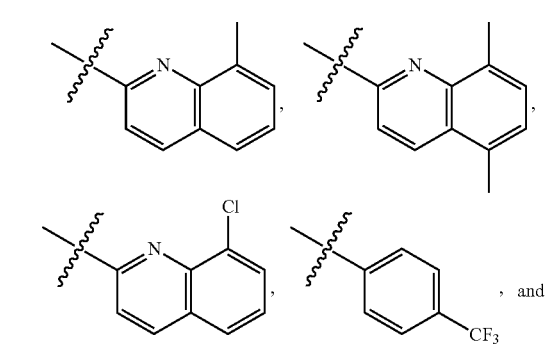

-continued

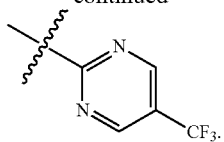

The present invention provides compounds according to Formula 2, or pharmaceutically acceptable salts thereof:

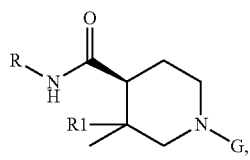

2 where: R1 is H or —CH$_3$; R is selected from:

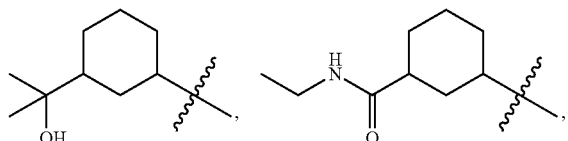

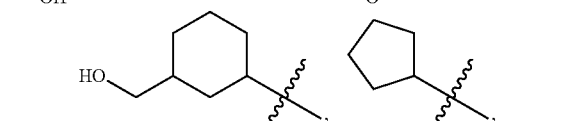

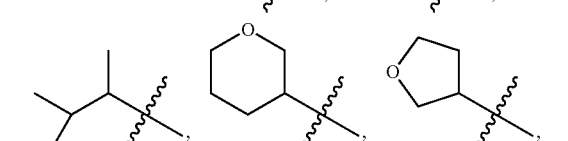

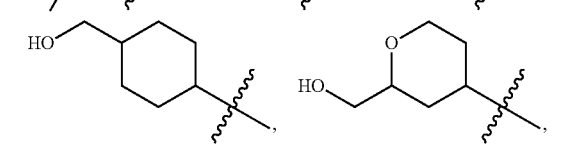

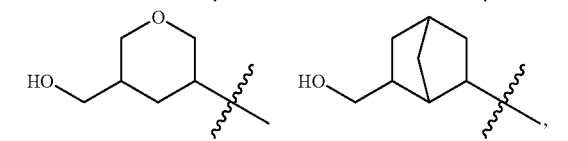

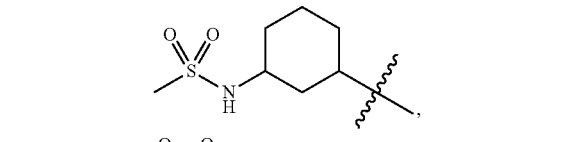

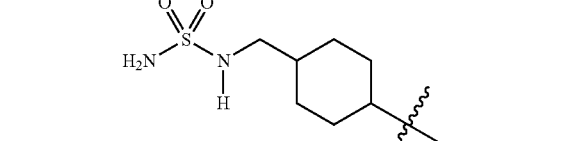

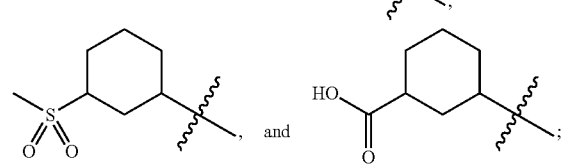

and

G is selected from:

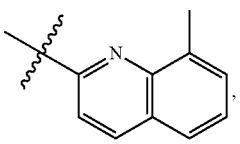

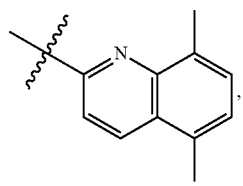

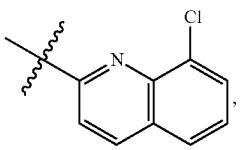

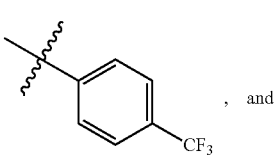

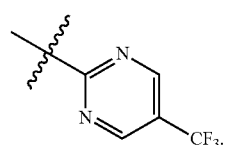

The present invention also provides compounds according to Formulae 1 or 2, or pharmaceutically acceptable salts thereof, where R1 is —CH$_3$.

For preferred compounds of Formulae 1 or 2, or pharmaceutically acceptable salts thereof, R is selected from:

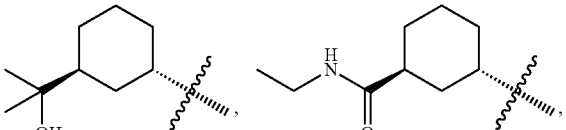

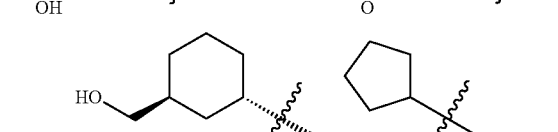

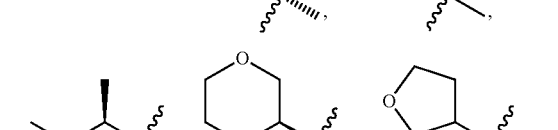

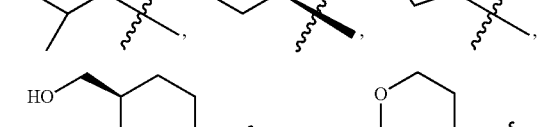

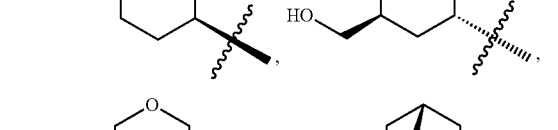

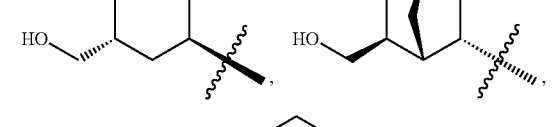

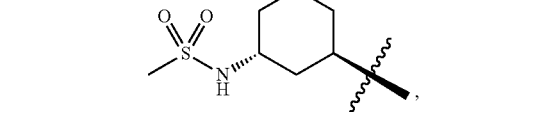

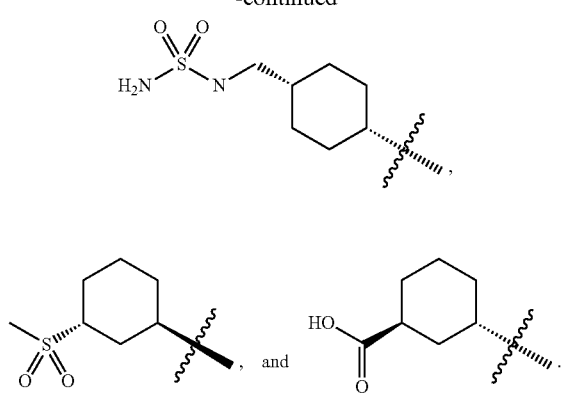

For more preferred compounds of Formulae 1 or 2, or pharmaceutically acceptable salts thereof, R is selected from:

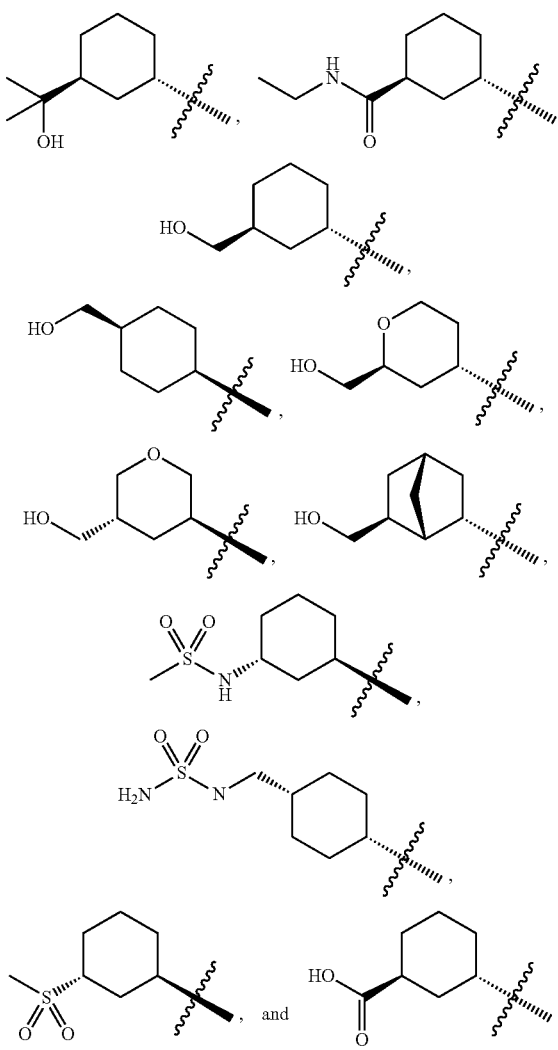

For still more preferred compounds of Formulae 1 or 2, or pharmaceutically acceptable salts thereof, R is selected from:

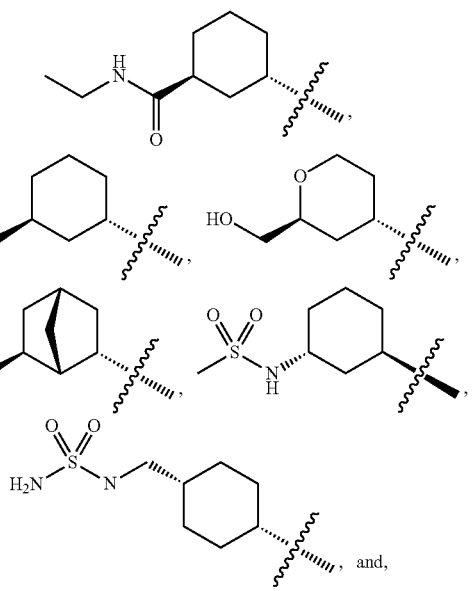

For preferred compounds of Formulae 1 or 2, or pharmaceutical salts thereof, G is:

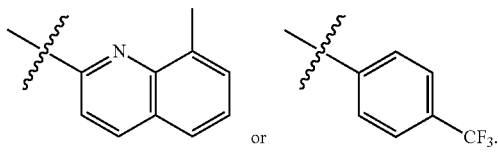

The present invention also provides a compound according to Formula 3, or a pharmaceutically acceptable salt thereof.

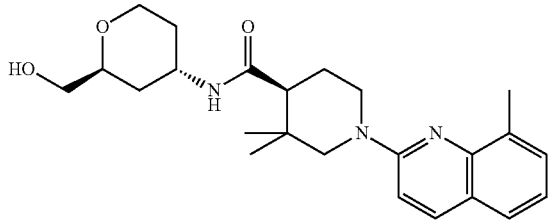 [SMILES: Cc1cccc2ccc(N3CC[C@H](C(=O)N[C@H]4CCO[C@H](CO)C4)C(C)(C)C3)nc12]

In one embodiment, compounds of Formulae 1, 2, or 3 are provided as a neutral species. In another embodiment, the compounds are provided as pharmaceutically acceptable salts. In one preferred salt form, the compound of Formula 3 is provided as hydrochloride salt.

The present invention also provides a pharmaceutically acceptable composition that includes a compound according Formulae 1, 2, or 3, or a pharmaceutically acceptable salt thereof, and at least one of a pharmaceutically acceptable carrier, diluent, or excipient.

The present invention also provides a method of treating a patient in need of treatment for pain associated with arthritis or osteoarthritis. The method comprises administering to the patient an effective amount of a pharmaceutically acceptable composition that includes a compound according Formulae 1, 2, or 3, or a pharmaceutically acceptable salt thereof, and at least one of a pharmaceutically acceptable carrier, diluent, or excipient.

The present invention also provides a method of treating a patient in need of treatment for arthritis or osteoarthritis. In one form, the present invention provides a method of treating a patient for the signs and/or symptoms of osteoarthritis. The method comprises administering to the patient an effective amount of a compound according to Formulae 1, 2, or 3, or a pharmaceutically acceptable salt thereof.

The present invention also provides a method of treating a patient in need of treatment for inflammation associated with arthritis or osteoarthritis. The method comprises administering to the patient an effective amount of a pharmaceutically acceptable composition that includes a compound according to Formulae 1, 2, or 3, or a pharmaceutically acceptable salt thereof, and at least one of a pharmaceutically acceptable carrier, diluent, or excipient.

The present invention also provides a method of treating a patient in need of treatment for pain associated with arthritis. The method comprises administering to the patient an effective amount of a compound according to Formulae 1, 2, or 3, or a pharmaceutically acceptable salt thereof. The present invention further provides a method of treating a patient for pain associated with osteoarthritis. The method comprising administering to the patient an effective amount of a compound according compound according to Formulae 1, 2, or 3, or a pharmaceutically acceptable salt thereof.

The present invention provides a compound according Formulae 1, 2, or 3 for use as a medicament. The medicament or compound can be used for therapy. The therapy can include the treatment of the patient for arthritis or osteoarthritis. In one embodiment the therapy can be the treatment of pain or inflammation associated with arthritis or osteoarthritis.

The present invention also provides the use of a compound for the manufacture of a medicament to treat arthritis or osteoarthritis. In one form, the medicament is used to treat pain or inflammation associated with arthritis or osteoarthritis.

As used herein, the terms "treating" or "to treat" includes stopping or reducing the severity of an existing symptom or disorder, in particular the pain and/inflammation, associated with arthritis or osteoarthritis.

As used herein, the term "patient" refers to a mammals, such as a guinea pigs, rats, dogs, cats, cows, horses, sheep, goats or humans; or fowl such as a chickens or ducks. The preferred patient is a mammal, more preferably a human.

The exemplified compounds of the present invention can be formulated into pharmaceutical compositions in accordance within accepted practices. Examples of pharmaceutically acceptable carriers, excipients, and diluents can be found in Remington's Pharmaceutical Sciences, Gennaro, Ed., Mack Publishing Co. Easton Pa. 1990. Non-limiting examples include the following: starch, sugars, mannitol, and silica derivatives; binding agents such as carboxymethyl cellulose and other cellulose derivatives, glycerol monostearate; adsorptive carriers such as kaolin and bentonite; and lubricants such as talc, calcium, and magnesium stearate, and solid polyethyl glycols. In one form, the pharmaceutical formulation includes 20% Captisol in 25 mM phosphate buffer pH 2.

Preferred pharmaceutical compositions can be formulated as a tablet or capsule for oral administration or as an injectable solution. The tablet, capsule, or solution will include a compound of the present invention in an amount effective for treating a patient in need of treatment.

As used herein, the term "effective amount" refers to the amount or dose of a compound of the invention, or a pharmaceutically acceptable salt thereof, which, upon a single or multiple dose administration to the patient, provides the desired effect, such as, the reduction or elimination of pain and/or inflammation the patient under diagnosis or treatment.

An effective amount can be readily determined by the attending diagnostician by using known techniques and by observing results obtained under analogous circumstances. In determining the effective amount for a patient, a number of factors can be considered by the attending diagnostician, including, but not limited to: the species of mammal, its size, age, and general health; the severity of the symptoms; the response of the individual patient; the mode of administration; the bioavailability characteristics of the compound of Formula 1, 2, or 3 or its pharmaceutically acceptable salt form, as a formulated drug product in the dose regimen selected; the use of concomitant medication; and other relevant circumstances.

In one embodiment, the effective amount can be from about 0.0005 mg/kg of body weight to about 100 mg/kg. More preferably, the effective amount can be from about 0.001 mg/kg to about 50 mg/kg. Still more preferably, the effective amount can be from about 0.001 mg/kg to about 20 mg/kg.

A compound of the present invention can be combined with other treatment methods and/or additional therapeutic agents. Preferably a compound of the present invention can be combined with other agents that also are effective for the treatment of arthritis or osteoarthritis. Examples of these additional therapeutic agents include: NSAIDs or COX-2 inhibitors such as ibuprofen, aspirin, acetaminophen, celecoxib, naproxen, and ketoprofen; opioids such as oxycodone, and fentanyl; and corticosteroids such as hydrocortisone, prednisolone, and prednisone.

The compound of the invention and the additional therapeutic agent(s) can be administered either together through the same delivery route and device such as a single pill, capsule tablet, or solution; or separately administered either at the same time in separate delivery devices or administered sequentially.

The compound of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The compound of the present invention, or a salt thereof, may be prepared by a variety of procedures known in the art, some of which are illustrated in the Schemes, Preparations, and Examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered or purified by conventional methods, including extraction, evaporation, precipitation, chromatography, supercritical fluid chromatography, filtration, trituration, and crystallization.

Individual isomers, enantiomers, or diastereomers may be separated or resolved by one of ordinary skill in the art at any convenient point in the synthesis of compounds of Formula 1 by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). Additionally, the intermediates described in the following preparations contain nitrogen and oxygen protecting groups. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

The reagents and starting materials are generally readily available to one of ordinary skill in the art. Others may be made by standard techniques of organic and heterocyclic chemistry and the procedures described in the Preparations and the Examples below.

The depiction of a bond with a line through it as illustrated below indicates the point of attachment of the substituent to the rest of the molecule.

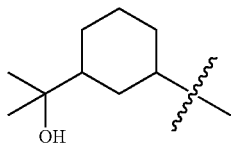

The abbreviations used herein are defined according to *Aldrichimica Acta*, Vol. 17, No. 1, 1984. Other abbreviations are defined as follows: "δ" refers to part per million downfield from tetramethylsilane; "ATCC" refers to American type culture collection; "BOP" refers to (benzotriazol-1-yloxy)tris(dimethylamino)phosphonium hexafluorophosphate; "BSA" refers to Bovine Serum Albumin; "CDI" refers 1,1'-carbonyldiimidazole; "DCC" refers to 1,3-dicyclohexylcarbodiimide; "DCM" refers to dichloromethane; "DIC" refers to 1,3-diisopropylcarbodiimide; "DMF" refers to dimethylformamide; "DMSO" refers to dimethylsulfoxide; "EDCI" refers to 1-(3-dimethylaminopropyl)-3-ethylcarbodiimide hydrochloride; "EDTA" refers to ethylenediaminetetraacetic acid; "ee" refers to enantiomer excess; "EIA" refers to enzyme immunoassay; "EIMS" refers to electron ionized mass spectrometry; "ESMS" refers to electrospray mass spectrometry; "EtOAc" refers to ethyl acetate; "EtOH" refers to ethanol or ethyl alcohol; "Ex. No." refers to Example Number; "HATU" refers to (1-[bis(dimethylamino)methylene]-1H-1,2,3-triazolo[4,5-b]pyridinium 3-oxid hexafluorophosphate); "HBTU" refers to (1H-benzotriazol-1-yloxy)(dimethylamino)-N,N-dimethylmethaniminium hexafluorophosphate; "HOAT" refers to 1-hydroxy-7-azobenzotriazole; "HOBT" refers to 1-hydroxybenzotriazole hydrate; "IC$_{50}$" refers to the concentration of an agent that produces 50% of the maximal inhibitory response possible for that agent; "i-PrOH" refers to isopropanol or isopropyl alcohol; "LPS" refers to lipopolysaccharide; "MeOH" refers to methanol; "min" refers to minutes; "NSAIDs" refers to nonsteroidal anti-inflammatory drugs; "PBS" refers to Phosphate Buffered Saline; "PGE$_2$" refers to prostaglandin E$_2$; "PGH$_2$" refers to prostaglandin H$_2$; "PGI$_2$" refers to prostaglandin I$_2$; "PyBOP" refers to (benzotriazol-1-yl-oxytripyrrolidinophosphonium hexafluorophosphate); "PyBrOP" refers to bromo(tri-pyrrolidinyl)phosphoniumhexafluorophosphate; "rhIL-1β" refers to recombinant human interleukin 1β; "SCF" refers to supercritical fluid; "SFC" refers to supercritical fluid chromatography; "TBME" refers to t-butyl ether methyl ether; "THF" refers to tetrahydrofuran; and "t$_R$" refers to retention time.

General LCMS Methods. All analyses are performed using an Agilent 1200 Infinity Series Liquid Chromatography (LC) system, consisting of a 1260 HiP degasser (G4225A), 1260 Binary Pump (G1312B), 1290 auto-sampler (G4226A), 1290 thermo-stated column compartment (G1316C) and a 1260 Diode Array Detector (G4212B) coupled to an Agilent 6150 single quadrupole mass spectrometry (MS) detector. The MS is operated with an electrospray ionization source (ESI) in both positive & negative ion mode. The nebulizer pressure is set to 50 psi, the drying gas temperature and flow to 350° C. and 12.0 L/min respectively. The capillary voltages used are 4000 V in positive mode and 3500 V in negative mode. Data acquisition is performed with Agilent Chemstation software.

HPLC Method 1. Analyses are carried out on a Daicel ChiralPak AD-3R column (100 mm length, 4.6 mm internal diameter, 3 µm particle size). The mobile phase used is: A2=Water with 10 mM ammonium bicarbonate, adjusted to pH 9 with ammonium hydroxide; and B2=acetonitrile. The run is performed at a temperature of 25° C. and a flow rate of 1.5 mL/min with a gradient elution from 50% to 95% (B2) over 3.0 min followed by a 3.0 min hold at 95% (B2). The UV (DAD) acquisition is performed at 40 Hz, with a scan range of 190-400 nm (by 5 nm step). A 1:1 flow split is used before the MS detector. The MS acquisition range is set to 100-800 m/z with a step size of 0.2 m/z in both polarity modes. Fragmentor voltage is set to 70 (ESI$^+$) or 120 (ESI$^-$), Gain to 0.40 (ESI$^+$) or 1.00 (ESI$^-$) and the ion count threshold to 4000 (ESI$^+$) or 1000 (ESI$^-$). The overall MS scan cycle time is 0.15 s/cycle.

SFC Method 1. Analyses are carried out on a Daicel ChiralPak OJ-H column (100 mm length, 4.6 mm internal diameter, 5 µm particle size). The mobile phase is: 8% (20 mM NH$_3$ in i-PrOH) and 92% CO$_{2(scf)}$ at a pressure of 100 bar. The run is performed at a temperature of 35° C. and a flow rate of 3 mL/minute. The UV (DAD) acquisition is performed at a wavelength of 220 nm.

SFC Method 2. Analyses are carried out on a Daicel ChiralPak AS-H column (100 mm length, 4.6 mm internal diameter, 5 µm particle size). The mobile phase is: 20% (20 mM NH$_3$ in i-PrOH) and 80% CO$_{2(scf)}$ at a pressure of 100 bar. The run is performed at a temperature of 35° C. and a flow rate of 5 mL/minute. The UV (DAD) acquisition is performed at a wavelength of 220 nm.

The following Schemes further illustrate the invention.

Scheme 1

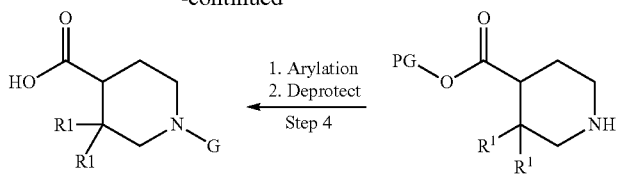

PG = protecting group

In Scheme 1, Step 1, a trifluoromethyl sulfonyl group is installed on the piperidine to act as a leaving group in the subsequent reaction of Step 2. "PG" is a protecting group developed for the amino group, such as carbamates and amides. The product of Step 1 is then subjected to carbonylation using a palladium catalyst to give the ester product of Step 2. The double bond in the tetrahydropyridine can be reduced under hydrogenation conditions. In Step 3, substep 2, the piperidine amine can be deprotected under acidic conditions. The piperidine product of Step 3 can then be reacted with a halogen substituted G group under conditions suitable for nucleophilic aromatic substitution give the product of Step 4. For example, an inorganic base such as $K_2CO_3$ or an organic base such as N,N-diisopropylethylamine, pyridine, or triethylamine can be used to give the product of Step 4, substep 1. Alternatively, the piperidine product of step 3 can be reacted with a quinolone N-oxide using an activating agent, such as PyProp, to give the product of Step 4. Deprotection of the piperidine carboxy group can be accomplished under standard conditions with an inorganic base such as aqueous sodium hydroxide or lithium hydroxide to give the product of Step 4, substep 2 or under acidic conditions using 4 M HCl or aqueous sulfuric acid.

Scheme 2

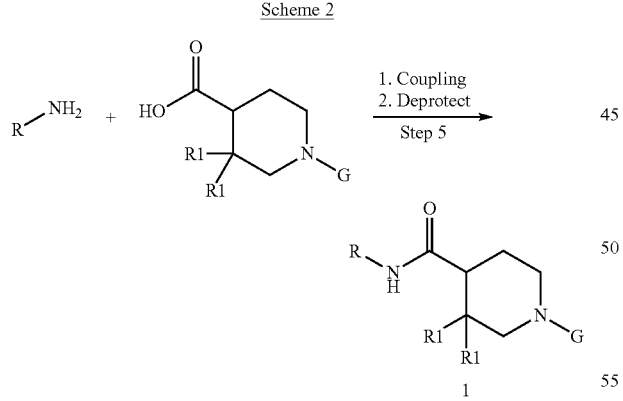

In Scheme 2, the piperidine carboxylic acid product of Step 4 can be coupled with an appropriate amine, R—NH₂, under amidation conditions using an organic base such as triethylamine or diisopropylethylamine, a coupling reagent such as EDCI, and a coupling additive such as HOBT to give the compounds of Step 5, substep 1. One skilled in the art will recognize that there are a number of methods and reagents for amide formation resulting from the reaction of carboxylic acids and amines. For example, the reaction of the amine compound with an appropriate carboxylic acid in the presence of a coupling reagent with or without an organic base can provide a compound of Formula 1. Coupling reagents include carbodiimides, such as DCC, DIC, EDCI or a carbonyldiimidazole such as CDI. Amide coupling additives, such as HOBT and HOAt can also be used to enhance the reaction. Additionally, uronium or phosphonium salts of non-nucleophilic anions, such as HBTU, HATU, BOP, PyBOP, and PyBrOP could be used in place of the more traditional coupling reagents. An additive such as DMAP may be used to enhance the reaction. The product of Step 5, substep 1 can then be deprotected, if necessary, under standard conditions with an inorganic base such as aqueous sodium hydroxide or lithium hydroxide in a solvent such as MeOH and THF to give compounds of Formula 1.

A pharmaceutically acceptable salt of the compounds of the invention, such as a hydrochloride salt, can be formed, for example by reaction of an appropriate free base of Formula 1 and an appropriate pharmaceutically acceptable acid, such as hydrochloric acid, in a suitable solvent such as diethyl ether under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The following Preparations and Examples further illustrate the invention.

Preparation 1 tert-Butyl 3,3-dimethyl-4-(((trifluoromethyl)sulfonyl)oxy)-3,6-dihydropyridine-1(2H)-carboxylate

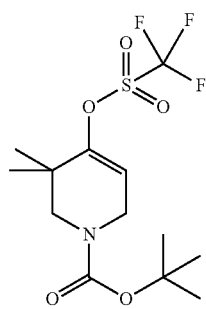 [SMILES: CC(C)(C)OC(=O)N1CC=C(OS(=O)(=O)C(F)(F)F)C(C)(C)C1]

Under a nitrogen atmosphere, cool a solution of diisopropylamine (260 mL, 1.85 mol) in THF (1.0 L) to −20° C. then add a solution of n-butyllithium (2.50 M in hexanes, 650 mL, 1.60 mol) drop-wise over 30 minutes. Allow the mixture to warm to −10° C. and stir for 1 hour. Cool the mixture to −74° C. and add a solution of tert-butyl 3,3-dimethyl-4-oxopiperidine-1-carboxylate (260 g, 1.14 mol) in THF (1.0 L mL) drop-wise over 60 minutes. Stir the mixture at −74° C. for 2 hours, and then add a solution of N-phenylbis (trifluoromethanesulfonimide) (430 g, 1.20 mol) in THF (1.0 L). Warm the mixture to 0° C. and stir for 2 hours. Allow the mixture to warm to room temperature and stir overnight. Quench the reaction with saturated aqueous NH₄Cl (1.0 L); dilute with water (2.0 L); separate the layers; and extract the aqueous layer with EtOAc (2×2 L). Combine the organic extracts; dry over Na₂SO₄; filter; collect the filtrate; and concentrate the filtrate under reduced pressure. Subject the resulting crude material to silica gel flash chromatography, eluting with a gradient of 0% to 15% TBME in hexanes, to provide the title compound as an orange oil in about 75% purity by mass as estimated by $^1$H NMR (430 g, 78%). $^1$H NMR (400 MHz, DMSO-d₆) δ 1.05 (s, 6H), 1.40 (s, 9H), 3.36 (s, 2H), 4.02 (d, J=3.4 Hz, 2H), 5.82 (br s, 1H).

Preparation 2

O1-tert-Butyl-O4-methyl 3,3-dimethyl-2,6-dihydropyridine-1,4-dicarboxylate

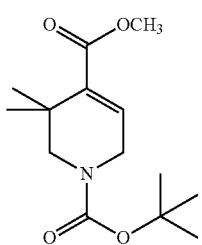 [SMILES: COC(=O)C1=CCN(C(=O)OC(C)(C)C)CC1(C)C]

Combine palladium(II) acetate (4.40 g, 20.0 mmol), 1,1'-bis(diphenylphosphino)ferrocene (13.3 g, 22.8 mmol), tert-butyl 3,3-dimethyl-4-(((trifluoromethyl)sulfonyl)oxy)-3,6-dihydropyridine-1(2H)-carboxylate (72.0 g, 150 mmol), anhydrous acetonitrile (850 mL), anhydrous MeOH (570 mL), and triethylamine (36.0 mL, 245 mmol) in a 2-L PARR™ autoclave fitted with a mechanical stirrer. Seal the autoclave. Purge and then pressurize the autoclave with carbon monoxide to 689 kPa. Heat the mixture to 65° C. for 2.25 hours; cool the mixture to room temperature; and carefully vent the autoclave. (Caution! Poison gas!). Concentrate under reduced pressure to give crude material. Combine this material with five other batches of material prepared by an analogous procedure on similar scales. Subject the combined material to silica gel flash chromatography, eluting with a gradient of 0% to 20% TBME in hexanes, to give the title compound as a yellow oil in about 83% purity by mass (260 g, 88%). MS (m/z): 214 (M−t-Bu+2H)⁺.

Preparation 3

(±)-O1-tert-Butyl-O4-methyl 3,3-dimethylpiperidine-1,4-dicarboxylate

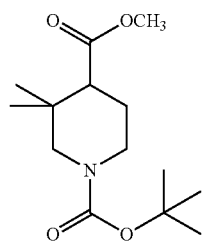 [SMILES: COC(=O)C1CCN(C(=O)OC(C)(C)C)CC1(C)C]

Suspend palladium (10 wt % on carbon, 5.4 g, 5.1 mmol) in MeOH (700 mL) then add a solution of O1-tert-butyl-O4-methyl 3,3-dimethyl-2,6-dihydropyridine-1,4-dicarboxylate (130 g, 396 mmol) dissolved in MeOH (700 mL) in a 2.25 L PARR™ reactor. Seal the reactor and purge it first with nitrogen gas then with hydrogen gas. Pressurize the reactor to 414 kPa with hydrogen and stir the mixture at room temperature for 1.5 hours. Release the pressure and filter the mixture to remove the catalyst. Combine the filtrate with that obtained from another essentially identical reaction and concentrate under reduced pressure to give the title compound as a yellow oil in about 85% purity by mass (240 g, 95%). MS (m/z): 216 (M−t-Bu+2H)⁺.

Preparation 4

(±)-Methyl 3,3-dimethylpiperidine-4-carboxylate hydrochloride

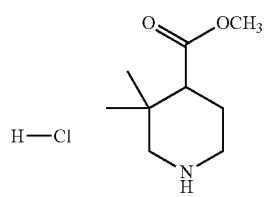

Add HCl (4.0 M solution in 1,4-dioxane, 2.0 L, 8.0 mol) to a solution of O1-tert-butyl-O4-methyl 3,3-dimethylpiperidine-1,4-dicarboxylate (240 g, 752 mmol) in 1,4-dioxane (500 mL). Stir the resulting mixture at room temperature overnight and concentrate under reduced pressure. Dilute the residue with TBME (500 mL) and collect the resulting solids by filtration. Rinse the filter cake with TBME (2×400 mL) and dry the solid in a vacuum oven at 35° C. overnight to give the title compound as a white solid (144 g, 92%). MS (m/z): 172 (M+H)⁺.

Preparation 5

(−)-Methyl (4S)-3,3-dimethyl-1-(8-methyl-2-quinolyl)piperidine-4-carboxylate

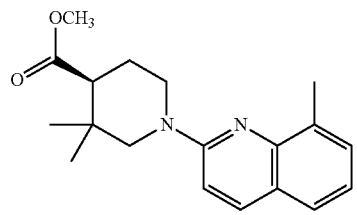 [SMILES: COC(=O)[C@H]1CCN(c2ccc3cccc(C)c3n2)CC1(C)C]

Add K$_2$CO$_3$ (210 g, 1.52 mol) to a mixture of methyl 3,3-dimethylpiperidine-4-carboxylate hydrochloride (144 g, 693 mmol) and 2-chloro-8-methylquinoline (125 g, 704 mmol) in DMSO (1.4 L). Stir the resulting mixture overnight at 131±1° C. Cool the mixture to room temperature; filter to remove the solids; collect the filtrate; dilute the filtrate with water (2 L); then extract with EtOAc (2×3 L). Wash the combined organic extracts with water (3×1.5 L); dry over Na$_2$SO$_4$; filter; collect and concentrate the filtrate under reduced pressure. Subject the resulting crude material to silica gel flash chromatography, eluting with a gradient of 25% to 30% (10% TBME in DCM) in hexanes, to provide the racemate of the title compound. Dissolve this material in MeOH (7.5 L) and filter. Subject the material to chiral SFC (Chiralpak OJ-H, 50 mm×250 mm×5 μm) using 15% (0.2% dimethylethylamine in i-PrOH) in CO$_{2(scf)}$ as the mobile phase at a flow rate of 400 g/min, by injecting 5 mL of solution every 95 seconds until all of the material has been subjected. For each injection, collect the first fraction to elute ($t_R$=2.57 min by SFC Method 1). Combine the collected fractions with those from a previous reaction prepared similarly to provide 98 g of crude methyl 3,3-dimethylpiperidine-4-carboxylate hydrochloride. Concentrate mixture under reduced pressure and recrystallize the material from hot EtOH (1.38 L). Collect the crystals and dry the crystalline material in a vacuum oven at 40° C. overnight to give the title compound as a white crystalline solid (156 g, 43% yield on a batch-proportional basis). MS (m/z): 313 (M+H)$^+$, [α]$^{20}_D$ −45° (c 0.21, DCM). ee=>99% as determined by SFC Method 1.

Preparation 6

(−)-(4S)-3,3-Dimethyl-1-(8-methyl-2-quinolyl)piperidine-4-carboxylic acid

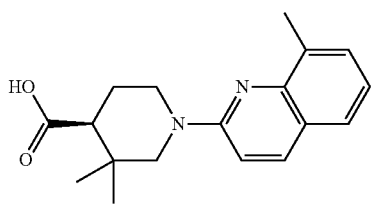 [SMILES: Cc1cccc2ccc(N3CC[C@H](C(=O)O)C(C)(C)C3)nc12]

Treat methyl (4S)-3,3-dimethyl-1-(8-methyl-2-quinolyl)piperidine-4-carboxylate (154 g, 493 mmol) with sulfuric acid (10% v/v in water, 2.31 L, 2.75 mol) and reflux the mixture overnight. Cool the mixture to room temperature and add NaOH (50 wt % in water) until the pH reaches 13. Add TBME (500 mL) to provide a triphasic mixture. Label the layers from top to bottom as: "Layer A," "Layer B," and "Layer C." Remove Layer C (the bottom layer). Add water (600 mL) to Layers A and B and separate the aqueous layer from the organic layers. Set aside the organic layers (A and B). Combine the aqueous layer with Layer C. Extract the combined aqueous layers with TBME (500 mL); separate the layers; and set aside the organic extracts. Add HCl (5.0 M) to the aqueous layer until the pH is 6.5. Extract the resulting aqueous mixture with TBME (2×400 mL). Combine all of the organic extracts (including Layers A and B); dry over MgSO$_4$; filter; collect and concentrate the filtrate under reduced pressure to give the title compound as a white solid in 96% purity (145 g, 95%). MS (m/z): 299 (M+H)±. [α]$^{20}_D$ −59.6° (c 3.12, CH$_3$OH).

Preparation 7

(±)-2-((Benzyloxy)methyl)-2,3-dihydro-4H-pyran-4-one

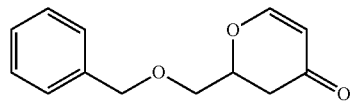 [SMILES: O=C1C=COC(COCc2ccccc2)C1]

Add a solution of ZnCl$_2$ in THF (0.5 M, 1.21 L, 607 mmol) to a cold (0° C.) solution of (E)-1-methoxy-3-(trimethylsilyl)oxy-1,3-butadiene (95% pure, 100 g, 551 mmol) and (benzyloxy)acetaldehyde (97% pure, 80 mL, 551.370 mmol) in toluene (551 mL) over 90 minutes while maintaining the internal temperature of the reaction mixture below 10° C. Allow the mixture to warm to room temperature and stir overnight. Divide the reaction mixture into two equal portions; perform the following procedures on each portion. Add trifluoroacetic acid (35 mL, 457 mmol) in four portions. After 20 minutes, concentrate the resulting mixture under reduced pressure; dilute with EtOAc; add excess saturated NaHCO$_3$; filter to remove the solids; collect the filtrate; separate and collect the organic layer. Wash the organic solution with saturated aqueous NaCl; isolate the organic extracts; dry over MgSO$_4$; filter; collect the filtrate; and concentrate under reduced pressure. Combine the resulting material from each of the previously separated portions. Subject the resulting material to silica gel flash chromatography, eluting with a gradient of 20% to 50% EtOAc in hexanes, to give the title compound as an orange oil in 92% purity (96 g, 73%). $^1$H NMR (400 MHz, CDCl$_3$) δ 7.40-7.28 (m, 6H), 5.42 (d, J=6.0 Hz, 1H), 4.65-4.56 (m, 3H), 3.74-3.67 (m, 2H), 2.75 (dd, J=16.8, 14.3 Hz, 1H), 2.42 (dd, J=16.9, 3.2 Hz, 1H).

Preparation 8

(±)-2-(Benzyloxymethyl)tetrahydropyran-4-one

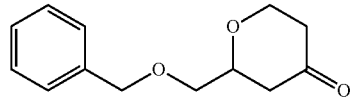 [SMILES: O=C1CCOC(COCc2ccccc2)C1]

Stir a mixture of EtOAc (880 mL), (±)-2-((benzyloxy)methyl)-2,3-dihydro-4H-pyran-4-one (96 g, 0.440 mol), triethylamine (123 mL, 0.882 mol), and palladium (10% on carbon, 4.68 g, 4.40 mmol) under an atmosphere of hydrogen at room temperature for 73 hours. Filter the mixture through diatomaceous earth; rinse the filter cake with EtOAc (250 mL); and sequentially wash the filtrate with aqueous HCl (0.1 M), saturated aqueous NaHCO$_3$, and saturated aqueous NaCl. Dry the organic layer over MgSO$_4$; filter; collect the filtrate; and concentrate under reduced pressure to give the title compound as a light yellow material (81.4 g, 84%). LC/MS (ESI$^+$): 221 [M+H]$^+$, 238 [M+NH$_4$]$^+$, 243 [M+Na]$^+$.

Preparation 9

(2S,4R)-2-(Benzyloxymethyl)tetrahydropyran-4-ol

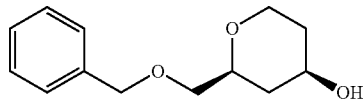 [SMILES: O[C@@H]1CCO[C@H](COCc2ccccc2)C1]

Cool a solution of (±)-2-(benzyloxymethyl)tetrahydropyran-4-one (40.6 g, 184 mmol) in THF (1.08 L) to −78° C. Add a solution of LiAlH$_4$ (1.0 M in THF, 240 mL, 240 mmol) drop-wise over 15 minutes. Allow the mixture to warm to 0° C. after the addition is complete and slowly add water (8.4 mL) drop-wise. After stirring the mixture for 5 minutes, add a solution of NaOH (15 mass % in water, 8.4 mL) and stir for an additional 5 minutes. Then add water (3×8.4 mL) and allow the mixture to warm to room temperature. After 30 minutes, filter the suspension to remove the solids and concentrate the filtrate under reduced pressure to provide the title compound as a colorless oil. Rinse the solids once with THF; filter; and concentrate the filtrate under reduced pressure. Combine this material with those obtained from previously reactions performed essentially according to the same procedure starting with 40 g, 22 g, and 45 g of (±)-2-(benzyloxymethyl)tetrahydropyran-4-one. Dissolve the combined material in i-PrOH (637 mL). Subject the material to chiral SFC (Chiralpak AS-H, 50 mm×150 mm×5 µm) using 25% i-PrOH in CO$_{2(scf)}$ as the mobile phase at a flow rate of 300 g/min, by injecting 1.35 g of solution every 114 seconds until all of the material has been injected. For each injection, collect the first fraction to elute (major isomer). Combine all of the collected fractions to give the title compound in >99% ee as determined by SFC Method 2 (62.8 g, 42% yield on a batch proportional basis). LC/MS (ESI): 223 [M+H]$^+$, 240 [M+NH$_4$]$^+$, 245 [M+Na]$^+$, 467 [2M+Na]$^+$.

Preparation 10

((2S,4R)-2-(Benzyloxymethyl)tetrahydropyran-4-yl)methanesulfonate

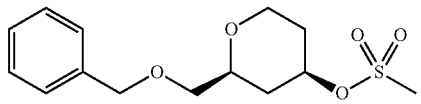 [SMILES: CS(=O)(=O)O[C@@H]1CCO[C@H](COCc2ccccc2)C1]

Drop-wise add a solution of methanesulfonyl chloride (11.7 mL, 150.6 mmol) in DCM (70 mL) to a mixture of (2S,4R)-2-(benzyloxymethyl)tetrahydropyran-4-ol (31 g, 139.5 mmol), DCM (1.40 L), and N,N-diisopropylethylamine (73.0 mL, 418.4 mmol) at 0° C. Allow the mixture to warm to room temperature and stir it overnight. Thereafter add a solution of methanesulfonyl chloride (0.537 mL, 6.98 mmol) in DCM (5 mL) and stir the mixture for 5 minutes at room temperature. Cool the mixture to 0° C., pour it into water; separate; and collect the organic layer. Wash the organic layer with water (500 mL); combine the organic layer with organic layers/extracts obtained from other, essentially identical reactions. Dry the combined organic solutions over MgSO$_4$; filter; collect the filtrate; and concentrate the filtrate under reduced pressure to give the title compound as a light orange oil (84.7 g, 97% yield on a batch proportional basis). $^1$H NMR (400 MHz, d$_6$-DMSO) δ 7.36-7.24 (m, 5H), 4.86-4.77 (m, 1H), 4.47 (s, 2H), 3.96 (dd, J=7.6, 4.4 Hz, 1H), 3.60-3.54 (m, 1H), 3.48-3.36 (m, 3H), 3.18 (s, 3H) 2.05 (d, J=7.8 Hz, 1H), 1.98 (d, J=7.8 Hz, 1H), 1.58 (app qd, J=12.0, 4.8 Hz, 1H), 1.40 (app q, J=11.8 Hz, 1H).

Preparation 11

((2S,4S)-4-Aminotetrahydro-2H-pyran-2-yl)methanol hydrochloride

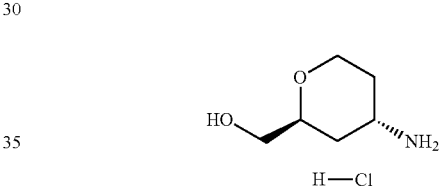

Add sodium azide (12.85 g, 191.7 mmol) to a solution of ((2S,4R)-2-(benzyloxymethyl)tetrahydropyran-4-yl)methanesulfonate (32.0 g, 106.5 mmol) in DMF (304 mL). Heat the resulting mixture to 100° C. and stir it for 4 hours. Cool the reaction mixture to room temperature. Pour the mixture into water (400 mL) and then extract with EtOAc (2×400 mL). Combine organic extracts and wash with saturated aqueous NaCl (3×200 mL). Dry the organic extracts over MgSO$_4$; filter; and collect the filtrate. Concentrate filtrate under reduced pressure to about 100 mL total volume. Dissolve resulting mixture in EtOAc (700 mL) and add it to a PARR™ vessel containing PtO$_2$ (2.7 g, 12 mmol) and EtOAc (700 mL). Purge the vessel with nitrogen; then pressurize it with hydrogen to 414 kPa. Agitate the mixture for 4 hours at room temperature. Filter the mixture and concentrate the colorless filtrate under reduced pressure to provide 23.2 g of a colorless oil. Combine with 36.2 g of material from a previous reaction prepared by essentially the same procedure. Dissolve the combined material in EtOH (600 mL) and add HCl (37 wt % in H$_2$O, 50 mL). Add the resulting mixture to a PARR™ vessel which contains Pd (10% on carbon, 10.0 g, 9.40 mmol) and EtOH (600 mL). Purge the reactor with nitrogen and pressurize it with hydrogen to 414 kPa. Agitate the mixture at room temperature for 1 hour. Filter the mixture; collect the filtrate; and concentrate the colorless filtrate under reduced pressure to give the title compound as a dark, thick oil in about 72% purity (54.2 g, 85%). LC/MS (ESI): 132 [M+H]$^+$.

Preparation 12

(±)-(Methyl 3,3-dimethyl-1-[4-(trifluoromethyl)phenyl]piperidine-4-carboxylate

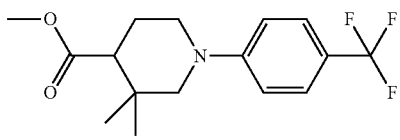

Add K$_2$CO$_3$ (460 mg, 3.33 mmol) to a mixture of methyl 3,3-dimethylpiperidine-4-carboxylate hydrochloride (300 mg, 1.44 mmol), 1-fluoro-4-(trifluoromethyl)benzene (475 mg, 2.89 mmol) and DMSO (2 mL). Stir the resulting mixture at 130° C. for 2 days. Cool the mixture to room temperature and stir for 3 days. Subject the resulting material to reverse-phase flash chromatography on C$_{18}$ silica gel, eluting with a gradient of 10% to 100% acetonitrile (0.1% formic acid) in water (0.1% formic acid), to give the title compound as a yellow oil (113 mg, 25%). MS (m/z): 316 (M+H)$^+$.

Preparation 13

(±)-3,3-Dimethyl-1-[4-(trifluoromethyl)phenyl]piperidine-4-carboxylic acid

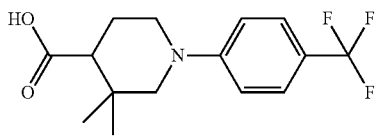 [SMILES: CC1(C)CN(c2ccc(C(F)(F)F)cc2)CCC1C(=O)O]

Add 2M aqueous NaOH (1 mL, 2 mmol) to a mixture of methyl (±)-3,3-dimethyl-1-[4-(trifluoromethyl)phenyl]piperidine-4-carboxylate (113 mg, 0.36 mmol), MeOH (1 mL), and THF (5 mL). Stir the resulting mixture at 50° C. overnight. Cool the mixture to room temperature, and add HCl (33 wt % in water) until the pH of the mixture is 3. Concentrate the mixture under reduced pressure to give the title compound as a yellow solid in 88% purity (123 mg, 99% yield). MS (m/z): 302 (M+H)$^+$.

Preparation 14

(±)-3,3-Dimethyl-1-[5-(trifluoromethyl)pyrimidin-2-yl]piperidine-4-carboxylic acid

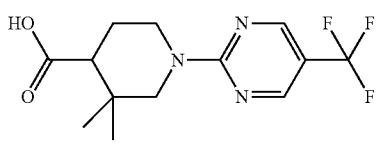 [SMILES: CC1(C)CN(c2ncc(C(F)(F)F)cn2)CCC1C(=O)O]

Add triethylamine (7.65 mL, 54.9 mmol) to a mixture of (±)-methyl 3,3-dimethylpiperidine-4-carboxylate hydrochloride (8.55 g, 41.2 mmol), 2-chloro-5-(trifluoromethyl)pyrimidine (5.0 g, 27.4 mmol), and acetonitrile (67 mL). Heat the mixture in a microwave to 180° C. for 1 hour; then cool the mixture to room temperature; and concentrate under reduced pressure. Add MeOH (40 mL), THF (80 mL), and 2 M aqueous NaOH (40 mL, 80 mmol). Stir the resulting mixture for 2 days at 50° C. Add 2 M aqueous NaOH (45 mL, 90 mmol) and stir the resulting mixture for 4 hours at 50° C. Cool the mixture to room temperature, and then add HCl (33 wt % in water) until the pH reaches 3. Concentrate under reduced pressure. Dilute with 1 N aqueous HCl (100 mL) and extract with EtOAc (2×100 mL). Wash the combined organic extracts with brine (100 mL); dry over Na$_2$SO$_4$; filter; collect the filtrate; and concentrate under reduced pressure to give the title compound (7.60 g, 61%). MS (m/z): 302 (M+H)$^+$.

Preparation 15

5,8-Dimethylquinoline-1-oxide

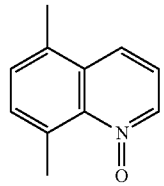

Add 3-chloroperoxybenzoic acid (5.96 g, 24.1 mmol) to a mixture of 5,8-dimethylquinoline (2 g, 12.1 mmol) and DCM (80 mL) maintained at 0° C. After 1 hour, add Na$_2$SO$_4$ (5 g) and filter the mixture. Collect the filtrate. Stir the resulting mixture at room temperature overnight. Dilute with DCM (100 mL); wash with 1 N aqueous NaOH (3×50 mL); dry over Na$_2$SO$_4$; filter; collect the filtrate; and concentrate to dryness under reduced pressure. Subject the resulting crude material to reverse-phase flash chromatography on C$_{18}$ silica gel, eluting with a gradient of 15% to 70% acetonitrile (10 mM ammonium bicarbonate) in water (10 mM ammonium bicarbonate) to give the title compound (372 mg, 18%). MS (m/z): 327 (M+H)$^+$.

Preparation 16

(±)-Methyl 1-(5,8-dimethyl-2-quinolyl)-3,3-dimethyl-piperidine-4-carboxylate

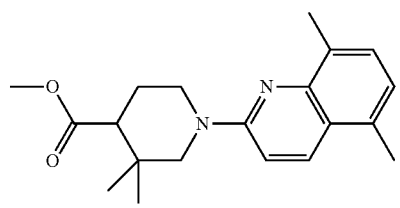

Add N,N-diisopropylethylamine (2.02 mL, 11.6 mmol) and PyBroP (1.75 g, 3.75 mmol) to a mixture of (±)-methyl 3,3-dimethylpiperidine-4-carboxylate hydrochloride (600 mg, 2.89 mmol), 5,8-dimethylquinoline-1-oxide (678 mg, 3.91 mmol), and DCM (15 mL). Stir the resulting mixture at room temperature for 3 days. Subject the crude reaction to reverse-phase flash chromatography on C$_{18}$ silica gel, eluting with a gradient of 10% to 100% acetonitrile (0.1% formic acid) in water (0.1% formic acid). Combine the fractions containing the desired product and concentrate under vacuum to approximately 30 mL volume. Adjust the pH to 6 with addition of a 1N aqueous NaOH solution. Extract the aqueous solution with EtOAc (2×30 mL), wash with a pH 6 aqueous buffer solution (4×30 mL), dry over MgSO$_4$; filter; and concentrate under reduced pressure to give the title compound (166 mg, 18%). MS (m/z): 327 (M+H)$^+$.

Preparation 17

(±)-1-(5,8-Dimethyl-2-quinolyl)-3,3-dimethyl-piperidine-4-carboxylic acid

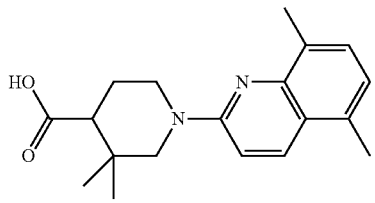 [SMILES: Cc1ccc(C)c2nc(N3CCC(C(=O)O)C(C)(C)C3)ccc12]

Combine a mixture of methyl (±)-1-(5,8-dimethyl-2-quinolyl)-3,3-dimethyl-piperidine-4-carboxylate (166 mg, 0.51 mmol), MeOH (0.1 mL), THF (0.5 mL), and 1 M aqueous NaOH (2.5 mL, 2.5 mmol) in a microwave vessel. Heat the resulting mixture at 120° C. for 2 hours in a microwave reactor. Cool the mixture to room temperature and add 1 N aqueous HCl until the pH is 6. Extract with CHCl$_3$ (2×25 mL); dry over Na$_2$SO$_4$; filter; collect the filtrate; and concentrate under reduced pressure to give the title compound (135 mg, 85%). MS (m/z): 312 (M+H)$^+$.

Preparation 18

(±)-Methyl 1-(8-chloro-2-quinolyl)-3,3-dimethyl-piperidine-4-carboxylate

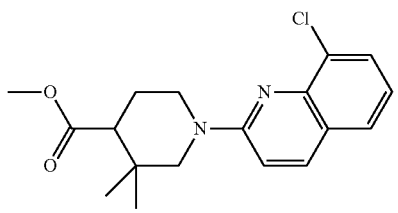 [SMILES: COC(=O)C1CCN(c2ccc3cccc(Cl)c3n2)CC1(C)C]

Add K$_2$CO$_3$ (1.07 g, 7.75 mmol) to a mixture of methyl (±)-3,3-dimethylpiperidine-4-carboxylate hydrochloride (700 mg, 3.37 mmol), 2,8-dichloroquinoline (876 mg, 4.38 mmol), and DMSO (4.5 mL). Stir the resulting mixture at 130° C. overnight. Cool the mixture to room temperature; filter to remove the solids; dilute with water (5 mL); and extract with EtOAc (4×20 mL). Wash the combined organic extracts with water (20 mL) then brine (20 mL). Dry the organic extracts over MgSO$_4$; filter; collect the filtrate; and concentrate under reduced pressure. Subject the resulting crude material to flash chromatography on silica gel, eluting with a gradient of 0% to 40% EtOAc in hexanes, to give the title compound (1.1 g, 98%). MS (m/z): 332 (M+H)$^+$.

Preparation 19

(±)-1-(8-Chloro-2-quinolyl)-3,3-dimethyl-piperidine-4-carboxylic acid

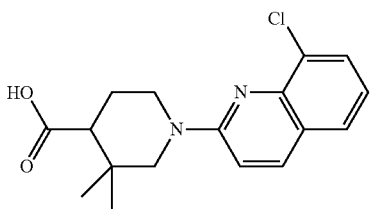 [SMILES: CC1(C)CN(c2ccc3cccc(Cl)c3n2)CCC1C(=O)O]

Combine a mixture of (±)-methyl 1-(8-chloro-2-quinolyl)-3,3-dimethyl-piperidine-4-carboxylate (1.1 g, 3.3 mmol), MeOH (0.8 mL), THF (3.3 mL), and 1 M aqueous NaOH (3.3 mL, 17 mmol) in a microwave vessel. Heat the resulting mixture at 120° C. for 2 hours in a microwave. Cool the mixture to room temperature and then add 5 N aqueous HCl until the pH is 6. Extract the mixture with EtOAc (3×10 mL). Combine the organic extracts; dry over Na$_2$SO$_4$; filter; collect the filtrate; and concentrate under reduced pressure to give the title compound (815 mg, 77%). MS (m/z): 318 (M+H)$^+$.

Preparation 20

Methyl 4-anilino-2,5-dihydrofuran-3-carboxylate

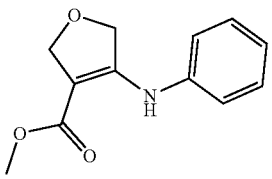 [SMILES: COC(=O)C1=C(Nc2ccccc2)COC1]

Add p-toluenesulfonic acid (500 mg, 3.16 mmol) to a mixture of (±)-methyl 4-oxotetrahydrofuran-3-carboxylate (6.6 g, 45.8 mmol), aniline (4.3 mL, 47.2 mmol) and toluene (70 mL). Fit the reaction vessel with a Dean-Stark trap and heat to 140° C. Stir the resulting mixture at room temperature overnight. Heat the reaction to 140° C. and stir for 2 hours. Cool the mixture and add diethyl ether (100 mL) and water (100 mL). Extract the mixture with diethyl ether (3×50 mL); dry over MgSO$_4$; filter; collect the filtrate; and concentrate under reduced pressure. Subject the resulting crude material to flash chromatography on silica gel, eluting with a gradient of 0% to 100% EtOAc in heptane, to give the title compound (6.7 g, 67%). MS (m/z): 220 (M+H)$^+$.

Preparation 21

(±)-Methyl-3-(iodomethyl)-4-phenylimino-tetrahydrofuran-3-carboxylate

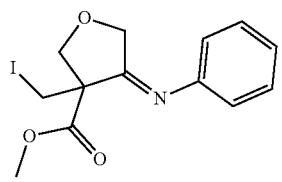 [SMILES: COC(=O)C1(CI)COC/C1=N\c1ccccc1]

Add a solution of (±)-methyl 4-anilino-2,5-dihydrofuran-3-carboxylate (3.6 g, 16.4 mmol) and 18-crown-6 (4.8 g, 18 mmol) in toluene (15 mL) to a mixture of potassium tert-butoxide (2.0 g, 17.8 mmol) and toluene (15 mL). Stir the resulting mixture at room temperature for 30 minutes. Add diiodomethane (4 mL) and stir the reaction at room temperature overnight. Add water (50 mL) and extract with diethyl ether (2×50 mL). Collect the organic extracts and wash with brine (50 mL). Dry the organic extracts over MgSO$_4$; filter; collect the filtrate; and concentrate under reduced pressure. Subject the resulting crude material to flash chromatography on silica gel, eluting with a gradient of 0% to 60% EtOAc in heptane, to give the title compound (1.0 g, 17%). MS (m/z): 359 (M+H)$^+$.

Preparation 22

(±)-Methyl 5-oxotetrahydropyran-3-carboxylate

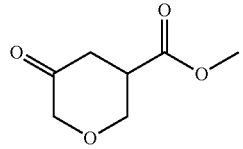

Heat a mixture of tri-n-butyltin hydride (1.12 mL, 4.18 mmol), 2,2'-azobis(2-methylpropionitrile) (35 mg, 0.21 mmol) and toluene (10 mL) to reflux. Add a solution of (±)-methyl-3-(iodomethyl)-4-phenylimino-tetrahydrofuran-3-carboxylate (1.0 g, 2.78 mmol) in toluene (50 mL) dropwise over three hours. Stir the resulting mixture at reflux for 3 hours. Concentrate the reaction under reduced pressure. Subject the resulting crude material to flash chromatography on silica gel, eluting with a gradient of 0% to 80% EtOAc in heptane, to give the title compound (0.37 g, 84%). $^1$H NMR (400 MHz, CDCl$_3$) δ 4.09-3.99 (m, 4H), 3.72 (s, 3H), 3.16 (m, 1H), 2.82 (dd, J=7.2, 16.9 Hz, 1H), 2.66 (dd, J=6.3, 16.9 Hz, 1H).

Preparation 23

(±)-Methyl trans-5-(benzylamino)tetrahydropyran-3-carboxylate

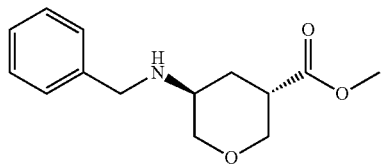 [SMILES: COC(=O)[C@@H]1COC[C@@H](NCc2ccccc2)C1]

Add sodium triacetoxyborohydride (0.96 g, 4.53 mmol) to a mixture of (±)-methyl 5-oxotetrahydropyran-3-carboxylate (0.33 g, 2.08 mmol), benzylamine (0.31 mL, 2.84 mmol) and 1,2-dichloroethane (5 mL). Stir the resulting mixture at room temperature for 2.5 hours. Add a saturated aqueous solution of sodium bicarbonate (10 mL); extract with DCM (3×10 mL); separate organic layer; wash with brine (10 mL); dry over MgSO$_4$; filter; collect the filtrate; and concentrate under reduced pressure. Subject the resulting crude material to flash chromatography on silica gel, eluting with a gradient of 0% to 60% EtOAc in heptane, to give the title compound (0.085 g, 16% yield). MS (m/z): 250 (M+H)$^+$.

Preparation 24

(±)-Methyl trans-5-aminotetrahydropyran-3-carboxylate

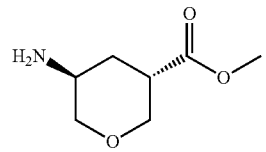

Add 10% palladium on carbon (0.07 g, 0.66 mmol) to a mixture of (±)-methyl trans-5-(benzylamino)tetrahydropyran-3-carboxylate (0.085 g, 0.34 mmol) and ethanol (8 mL). Purge the mixture with hydrogen and stir the resulting mixture at room temperature under hydrogen (1 atm) overnight. Filter the mixture and concentrate under reduced pressure to give the title compound (0.045 g, 83% yield). $^1$H NMR (400 MHz, CDCl$_3$) δ 3.82-3.77 (m, 2H), 3.68 (m, 4H), 3.38-3.31 (m, 1H), 3.11-3.08 (m, 1H), 2.85-2.80 (m, 1H), 2.17-2.11 (m, 1H), 1.78-1.71 (m, 3H).

Preparation 25

(±)-Methyl trans-5-[[(4S)-3,3-dimethyl-1-(8-methyl-2-quinolyl)piperidine-4-carbonyl]amino]tetrahydropyran-3-carboxylate

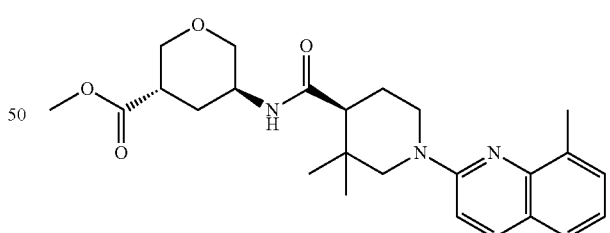

Add EDCI (0.087 g, 0.45 mmol) to a mixture of (−)-(4S)-3,3-dimethyl-1-(8-methyl-2-quinolyl)piperidine-4-carboxylic acid (0.087 g, 0.29 mmol), (±)-methyl-trans-5-aminotetrahydropyran-3-carboxylate (0.045 g, 0.28 mmol), HOBT (9 mg, 0.06 mmol), triethylamine (0.15 mL, 1.08 mmol), in DCM (5 mL). Stir the resulting mixture at room temperature for 3 hours. Subject the resulting mixture to flash chromatography on silica gel, eluting with a gradient of 5% to 100% EtOAc in heptane, to give the title compound (0.085 g, 66%). MS (m/z): 439 (M+H)$^+$.

Preparation 26

(±)-Methyl trans-3-(dibenzylamino)cyclohexanecarboxylate

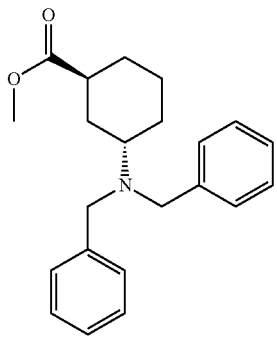 [SMILES: COC(=O)[C@H]1CCC[C@H](N(Cc2ccccc2)Cc2ccccc2)C1]

Add potassium carbonate (3.53 g, 25.6 mmol) and benzyl bromide (1.9 mL, 15.9 mmol) to a mixture of (±)-methyl-trans-3-aminocyclohexanecarboxylate (1.07 g, 6.8 mmol) in acetonitrile (40 mL). Heat the resulting mixture to 80° C. and stir for 5 hours. Cool the mixture and add acetonitrile (40 mL). Filter through diatomaceous earth and concentrate the filtrate under reduced pressure. Subject the resulting crude material to flash chromatography on silica gel, eluting with a gradient of 0% to 20% EtOAc in hexanes, to give the title compound (1.6 g, 70%). MS (m/z): 338 (M+H)$^+$.

Preparation 27

(±)-2-[trans-3-(Dibenzylamino)cyclohexyl]propan-2-ol

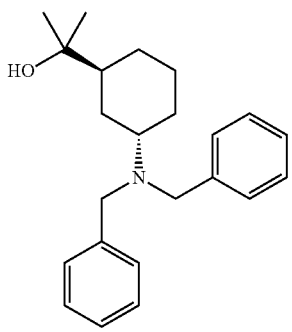 [SMILES: CC(C)(O)[C@H]1CCC[C@H](N(Cc2ccccc2)Cc2ccccc2)C1]

Add methylmagnesium bromide (3.0 M solution in diethyl ether, 16 mL, 48 mmol) to a mixture of (±)-methyl-trans-3-(dibenzylamino)cyclohexanecarboxylate (1.6 g, 4.7 mmol) and THF (50 mL), maintained at 0° C. Allow the reaction to warm to room temperature and stir overnight. Add water (25 mL) and filter through diatomaceous earth. Collect the aqueous filtrate. Extract the resulting aqueous material with EtOAc (50 mL). Collect the organic extracts; dry over Na$_2$SO$_4$; filter; collect the filtrate; and concentrate under reduced pressure. Add EtOAc (50 mL); wash with saturated aqueous NH$_4$Cl (2×25 mL); dry over Na$_2$SO$_4$; filter; collect the filtrate; and concentrate under reduced pressure to give the title compound (1.1 g, 69%). MS (m/z): 338 (M+H)$^+$.

Preparation 28

2-[(1S,3S)-3-(Dibenzylamino)cyclohexyl]propan-2-ol

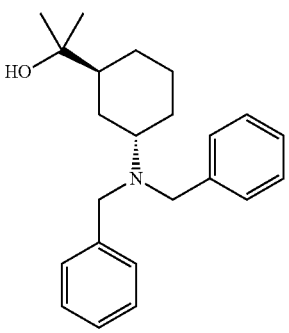 [SMILES: CC(C)(O)[C@H]1CCC[C@H](N(Cc2ccccc2)Cc2ccccc2)C1]

Dissolve (±)-2-[trans-3-(dibenzylamino)cyclohexyl]propan-2-ol (1.1 g, 3.26 mmol) in ethanol (13 mg/mL). Subject the material to chiral SFC (Chiralpak IA, 2 cm×15 cm) using 12% (0.1% dimethylethylamine in i-PrOH) in CO$_{2(scf)}$ as the mobile phase at 220 nm and a flow rate of 70 mL/minute. Collect and combine the first fraction to elute and concentrate under reduced pressure, to provide the title compound (0.54 g, 49%), ee=>99%. MS (m/z): 338 (M+H)$^+$. SFC Analytical method (Chiralpak IA, (15 cm×0.46 cm) using 10% (0.1% dimethylethylamine in i-PrOH) in CO$_{2(scf)}$ as the mobile phase at 220 nm and a flow rate of 3 mL/minutes).

Preparation 29

2-[(1S,3S)-3-Aminocyclohexyl]propan-2-ol hydrochloride

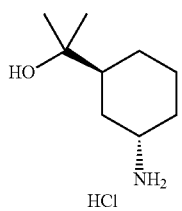

Add palladium hydroxide (20% on carbon, 0.51 g, 3.7 mmol) to a mixture of 2-[(1S,3S)-3-(dibenzylamino)cyclohexyl]propan-2-ol (0.54 g, 1.6 mmol) in MeOH (20 mL) in a Parr™ shaker vessel. Purge and pressurize the vessel with hydrogen to 414 kPa. Shake mixture for 4 days at room temperature. Filter the mixture through diatomaceous earth and concentrate the filtrate under reduced pressure. Dilute the mixture in diethyl ether (25 mL) and DCM (25 mL). Add HCl (4.0 M solution in 1,4-dioxane, 0.8 mL) and concentrate under reduced pressure to give the title compound (0.24 g, 77%). MS (m/z): 158 (M+H)$^+$.

Preparation 30 tert-Butyl N-[(1RS,2RS,4SR,6RS)-6-(hydroxymethyl)norbornan-2-yl]carbamate

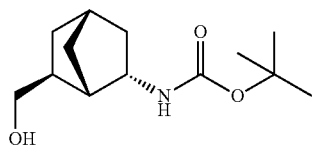 [SMILES: CC(C)(C)OC(=O)N[C@H]1C[C@H]2C[C@H](CO)[C@@H]1C2]

Combine (acetylacetonato)dicarbonylrhodium (10 mg, 0.03 mmol), 1,1'-bis(diphenylphosphino)ferrocene (27 mg, 0.05 mmol), methyl bicyclo[2.2.1]hept-2-ene-5-carboxylate (2.5 g, 11.9 mmol) and tert-butanol (25 mL) to a PARR™ autoclave with mechanical stirrer. Purge and pressurize the vessel with Syngas (1:1 mix of carbon monoxide and hydrogen, 310 kPa). Stir overnight. Concentrate the mixture under reduced pressure. Dilute in DCM (29 mL) and MeOH (2.9 mL). Add sodium borohydride (0.26 g, 6.9 mmol) and stir for 20 min at room temperature. Add DCM (60 mL) and wash with saturated aqueous sodium carbonate (2×25 mL) and brine (25 mL). Dry the organic layer over $Na_2SO_4$; filter; collect the filtrate; and concentrate under reduced pressure. Subject the resulting crude material to flash chromatography on silica gel eluting with a solution of 30% DCM, 30% tert-butyl methyl ether and 40% hexanes, to give the title compound as a mixture of diastereomers (0.58 g, 21%). $^1$H NMR (400 MHz, $CDCl_3$) δ 4.71-4.59 (m, 1H), 3.92-3.81 (m, 1H), 3.46-3.45 (m, 2H), 2.36 (d, J=3.0 Hz, 1H), 2.21-2.05 (m, 3H), 1.55 (br s, 1H), 1.49-1.25 (m, 12H), 1.16-1.09 (m, 1H), 0.68 (ddd, J=12.9, 4.5, 2.4 Hz, 1H).

Preparation 31

[(1RS,2RS,4SR,6RS)-6-Aminonorbornan-2-yl]methanol hydrochloride

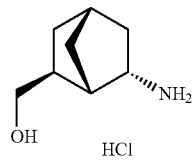

Add HCl (4.0 M solution in 1,4-dioxane, 2.1 mL, 8.3 mmol) to a mixture of tert-butyl N-[(1RS,2RS,4SR,6RS)-6-(hydroxymethyl)norbornan-2-yl]carbamate (0.2 g, 0.83 mmol) in DCM (8 mL) maintained at 0° C. Allow the resulting mixture to warm to room temperature and stir for 3 hours. Concentrate the mixture under reduced pressure to give the title compound (0.15 g, 100%). $^1$H NMR (400 MHz, $CDCl_3$) δ 8.17-8.02 (m, 3H), 4.93-4.90 (br, 1H), 3.47-3.45 (m, 1H), 3.19-3.15 (m, 2H), 2.31 (m, 1H), 2.14-2.12 (m, 1H), 2.01-1.94 (m, 1H), 1.92-1.88 (m, 1H), 1.44-1.35 (m, 2H), 1.22 (m, 1H), 1.04-0.98 (m, 2H).

Preparation 32 tert-Butyl ((cis-4-((tert-butoxycarbonyl)amino)cyclohexyl)methyl)(sulfamoyl)carbamate

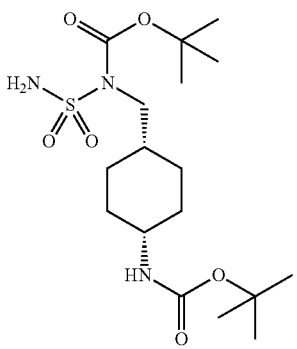 [SMILES: CC(C)(C)OC(=O)N[C@H]1CC[C@@H](CN(C(=O)OC(C)(C)C)S(N)(=O)=O)CC1]

Add diisopropyl azodicarboxylate (1.6 mL, 7.8 mmol) to a mixture of tert-butyl cis-4-(hydroxymethyl)cyclohexylcarbamate (1.5 g, 6.5 mmol), tert-butyl N-sulfamoylcarbamate (1.9 g, 9.8 mmol), triphenylphosphine (2.1 g, 7.8 mmol), and EtOAc (33 mL). Stir overnight at room temperature. Add water (50 mL); extract with EtOAc (2×50 mL); collect the organic extracts. Wash the organic extracts with brine (25 mL); dry over $MgSO_4$; filter; collect the filtrate; and concentrate under reduced pressure. Subject the resulting crude material to flash chromatography on silica gel, eluting with a gradient of 10% to 80% EtOAc in hexane, to give the title compound (1.78 g, 67%). MS (m/z): 430 $(M+Na)^+$.

Preparation 33 cis-1-amino-4-[(sulfamoylamino)methyl]cyclohexane hydrochloride

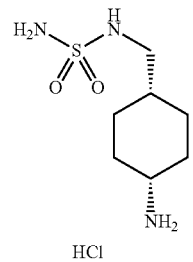 [SMILES: NS(=O)(=O)NC[C@H]1CC[C@@H](N)CC1 ; Cl]

Add HCl (4.0 M solution in 1,4-dioxane, 15 mL, 60 mmol) to tert-butyl ((cis-4-((tert-butoxycarbonyl)amino)cyclohexyl)methyl)(sulfamoyl)carbamate (1.78 g, 4.37 mmol). Stir the resulting mixture overnight at room temperature. Concentrate under reduced pressure. Dilute in MeOH (10 mL) and add drop-wise diethyl ether (150 mL) while vigorously stirring. Collect the resulting white precipitate by vacuum filtration to give the title compound (0.68 g, 56%). MS (m/z): 208 $(M+H)^+$.

Preparation 34

Methyl (1RS,3RS)-3-((S)-3,3-dimethyl-1-(8-methylquinolin-2-yl)piperidine-4-carboxamido)cyclohexane-1-carboxylate

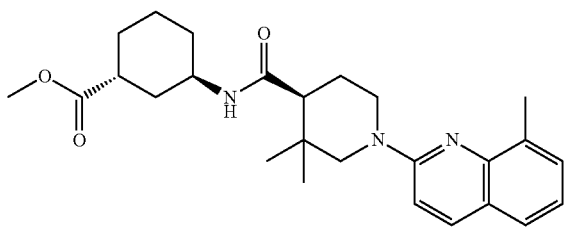 [SMILES: COC(=O)[C@@H]1CCC[C@@H](NC(=O)[C@H]2CCN(c3ccc4cccc(C)c4n3)CC2(C)C)C1]

Add triethylamine (0.9 mL, 7 mmol) to a mixture of (−)-(4S)-3,3-dimethyl-1-(8-methyl-2-quinolyl)piperidine-4-carboxylic acid (0.8 g, 3 mmol), (±)-methyl trans-3-aminocyclohexanecarboxylate hydrochloride (0.5 g, 3 mmol), BOP (2.0 g, 3 mmol) and DMF (5 mL). Stir the resulting mixture at room temperature overnight. Add a saturated aqueous solution of sodium bicarbonate (20 mL) and extract with EtOAc (2×25 mL). Collect the organic extracts; wash with brine (25 mL); dry over MgSO₄; filter; collect the filtrate; and concentrate under reduced pressure. Subject the resulting crude material to flash chromatography on silica gel, eluting with a gradient of 10% to 90% EtOAc in hexanes, to give the title compound (1.00 g, 80%). MS (m/z): 438 (M+H)⁺.

EXAMPLE 1

(S)-N-((2S,4S)-2-(Hydroxymethyl)tetrahydro-2H-pyran-4-yl)-3,3-dimethyl-1-(8-methylquinolin-2-yl)piperidine-4-carboxamide

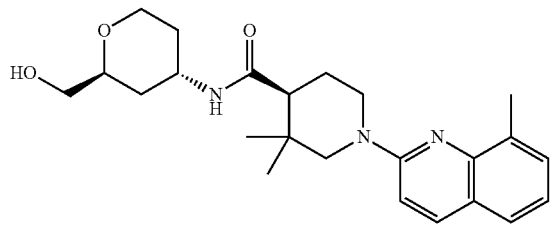 [SMILES: Cc1cccc2ccc(N3CC[C@H](C(=O)N[C@H]4CCO[C@H](CO)C4)C(C)(C)C3)nc12]

Add benzotriazol-1-yl-oxytripyrrolidinophosphonium hexafluorophosphate (153 g, 293 mmol) as a slurry in DMF (152 mL) to a cold (10° C.) mixture of (−)-(4S)-3,3-dimethyl-1-(8-methyl-2-quinolyl)piperidine-4-carboxylic acid (76.0 g, 245 mmol), ((2S,4S)-4-aminotetrahydro-2H-pyran-2-yl)methanol hydrochloride (72% pure, 57.37 g, 246 mmol), triethylamine (153 mL, 1.10 mol), and DMF (380 mL) while maintaining the internal reaction temperature below 20° C. Thereafter allow the mixture to warm to room temperature and stir it for 30 minutes. Pour the mixture into ice water (1.5 L) while stirring it. Extract the mixture with DCM (2×600 mL) and wash the combined organic extracts with a half-saturated aqueous NaCl solution (1.0 L). Dry the organic solution over MgSO₄; filter; collect the filtrate; and concentrate the filtrate under reduced pressure to give a wet solid. Triturate the wet solid with water and isolate the solid by filtration. Triturate the solid again with water (1.5 L) and isolate the solid by filtration. Wash the solid with water (2×250 mL). Set this first batch of isolated solid aside. Collect the aqueous washings; extract with DCM (2×800 mL); combine the DCM extracts. Add the first batch of isolated solids to the combined DCM extracts and wash with aqueous HCl (2.5 M, 2×800 mL). Separate the aqueous layer and add 50% aqueous NaOH solution to the aqueous layer until the pH reaches 12 to induce precipitation. Filter the mixture to collect the resulting solid. Rinse the solid with water (2×300 mL). Dry the solid in a vacuum oven at 50° C. for 3 hours. Dissolve the solid in MeOH (1.2 L); add mercaptopropyl mesoporous silica scavenging resin (1.2 mmol/g, 715 m²/g, 54 μm average particle size); and stir at 50° C. overnight. Filter to remove the solids collecting the filtrate. Rinse the solid with 1:1 CH₂Cl₂:MeOH (2×500 mL). Combine the filtrates and concentrate under reduced pressure to give a white solid. Triturate the solid with TBME (1.5 L), and collect the solids. Crystallize the solid from hot EtOH (1.8 L). Dry the solid in a vacuum oven at 50° C. for 2.5 hours to give the title compound as a crystalline, white solid (76.7 g, 76%). LC/MS (ESI): 412 [M+H]⁺.

The following Examples in Table 1 can be prepared essentially by the procedure of Preparation 34 using the appropriate starting amine in place of (±)-methyl-trans-3-aminocyclohexanecarboxylate hydrochloride and the appropriate starting carboxylic acid in place of (−)-(4S)-3,3-dimethyl-1-(8-methyl-2-quinolyl)piperidine-4-carboxylic acid.

TABLE 1

| Ex. No. | Structure | Chemical Name | MS (m/z) (M + H) | Purif.-Meth |
|---|---|---|---|---|
| 2 | 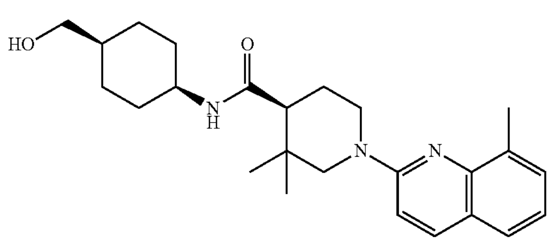 [SMILES: Cc1cccc2ccc(N3CC[C@H](C(=O)N[C@H]4CC[C@@H](CO)CC4)C(C)(C)C3)nc12] | (4S)-N-[4-(Hydroxymethyl)-cis-cyclohexyl]-3,3-dimethyl-1-(8-methyl-2-quinolyl)piperidine-4-carboxamide | 410 | A |

TABLE 1-continued

| Ex. No. | Structure | Chemical Name | MS (m/z) (M + H) | Purif.-Meth |
|---|---|---|---|---|
| 3 | 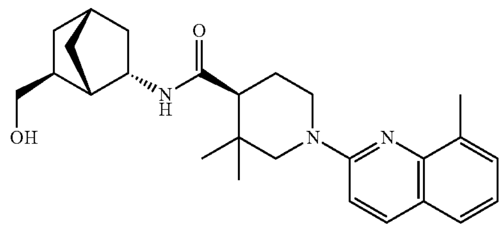 [SMILES: Cc1cccc2ccc(N3CC[C@H](C(=O)N[C@H]4C[C@H]5C[C@H](CO)[C@@H]4C5)C(C)(C)C3)nc12] | (4S)-N-[6-(1S,2S,4R,6S)-(Hydroxymethyl)norbornan-2-yl]-3,3-dimethyl-1-(8-methyl-2-quinolyl)piperidine-4-carboxamide | 422 | B |
| 4 | 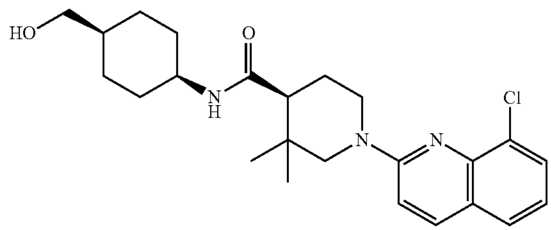 [SMILES: CC1(C)CN(c2ccc3cccc(Cl)c3n2)CC[C@@H]1C(=O)N[C@H]1CC[C@@H](CO)CC1] | (4S)-1-(8-Chloro-2-quinolyl)-N-[4-(hydroxymethyl)-cis-cyclohexyl]-3,3-dimethyl-piperidine-4-carboxamide | 430 | A |
| 5 | 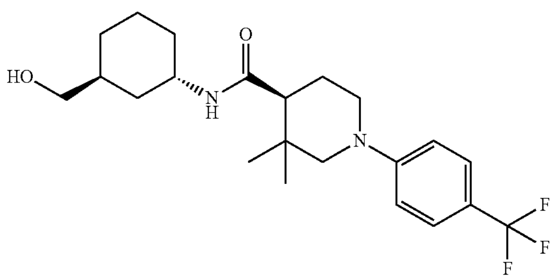 [SMILES: CC1(C)CN(c2ccc(C(F)(F)F)cc2)CC[C@@H]1C(=O)N[C@H]1CCC[C@H](CO)C1] | (4S)-N-[(1S,3S)-3-(Hydroxymethyl)cyclohexyl]-3,3-dimethyl-1-[4-(trifluoromethyl)phenyl]-piperidine-4-carboxamide | 413 | C |
| 6 | 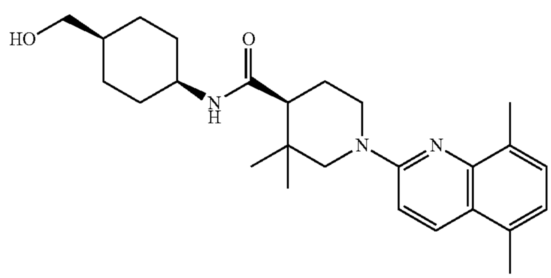 [SMILES: Cc1ccc(C)c2nc(N3CC[C@H](C(=O)N[C@H]4CC[C@@H](CO)CC4)C(C)(C)C3)ccc12] | (4S)-1-(5,8-Dimethyl-2-quinolyl)-N-[4-(hydroxymethyl)-cis-cyclohexyl]-3,3-dimethyl-piperidine-4-carboxamide | 424 | B |
| 7 | 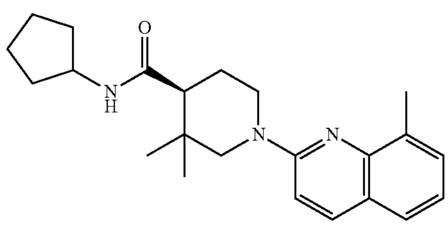 [SMILES: Cc1cccc2ccc(N3CC[C@H](C(=O)NC4CCCC4)C(C)(C)C3)nc12] | (4S)-N-Cyclopentyl-3,3-dimethyl-1-(8-methyl-2-quinolyl)piperidine-4-carboxamide | 366 | B |

TABLE 1-continued

| Ex. No. | Structure | Chemical Name | MS (m/z) (M + H) | Purif.-Meth |
|---|---|---|---|---|
| 8 | 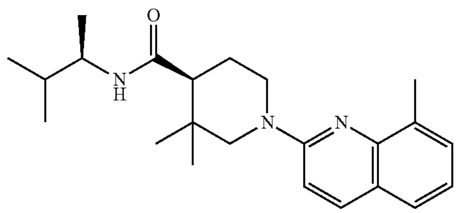 [SMILES: Cc1cccc2ccc(N3CC[C@H](C(=O)N[C@H](C)C(C)C)C(C)(C)C3)nc12] | (4S)-N-[(1R)-1,2-Dimethylpropyl]-3,3-dimethyl-1-(8-methyl-2-quinolyl)-piperidine-4-carboxamide | 368 | B |
| 9 | 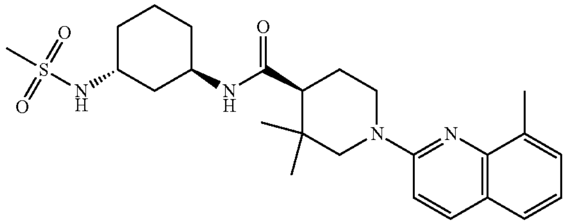 [SMILES: Cc1cccc2ccc(N3CC[C@H](C(=O)N[C@@H]4CCC[C@@H](NS(C)(=O)=O)C4)C(C)(C)C3)nc12] | (4S)-N-[3-(1S,3S)-(Methanesulfonamido)-cyclohexyl]-3,3-dimethyl-1-(8-methyl-2-quinolyl)piperidine-4-carboxamide | 473 | B |
| 10 | 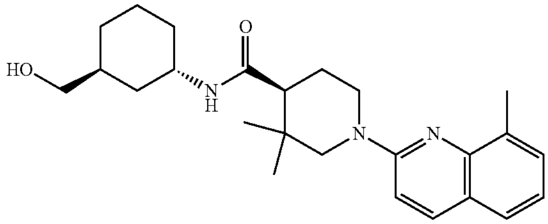 [SMILES: Cc1cccc2ccc(N3CC[C@H](C(=O)N[C@H]4CCC[C@H](CO)C4)C(C)(C)C3)nc12] | (4S)-N-[3-(1S,3S)-(Hydroxymethyl)cyclohexyl]-3,3-dimethyl-1-(8-methyl-2-quinolyl)piperidine-4-carboxamide | 410 | A |
| 11 | 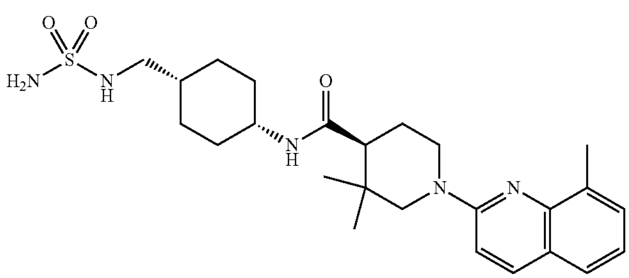 [SMILES: Cc1cccc2ccc(N3CC[C@H](C(=O)N[C@H]4CC[C@@H](CNS(N)(=O)=O)CC4)C(C)(C)C3)nc12] | (4S)-3,3-Dimethyl-1-(8-methyl-2-quinolyl)-N-[4-cis-[(sulfamoylamino)methyl]-cyclohexyl]piperidine-4-carboxamide | 488 | A |
| 12 | 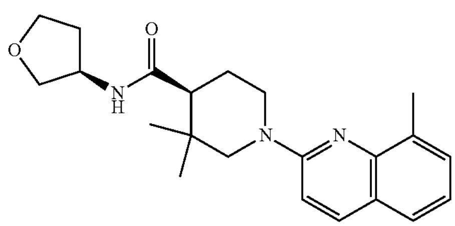 [SMILES: Cc1cccc2ccc(N3CC[C@H](C(=O)N[C@@H]4CCOC4)C(C)(C)C3)nc12] | (4S)-3,3-Dimethyl-1-(8-methyl-2-quinolyl)-N-[(3R)-tetrahydrofuran-3-yl]piperidine-4-carboxamide | 368 | A |

Purification Methods (Purif Meth): A=Crude product is purified by silica gel normal phase column chromatography eluting with gradient of EtOAc in hexanes. B=Crude product is purified by C18 reverse phase column chromatography eluting with a gradient of acetonitrile and water. C=Crude product is purified by chiral column chromatography with Chiralpak AS-H, 21×150 mm) using 15% IPA in $CO_2$ as the mobile phase at a flow rate of 70 mL/min.

EXAMPLE 13

(4S)-N-[(1S,3S)-3-(1-Hydroxy-1-methyl-ethyl)cyclohexyl]-3,3-dimethyl-1-(8-methyl-2-quinolyl)piperidine-4-carboxamide

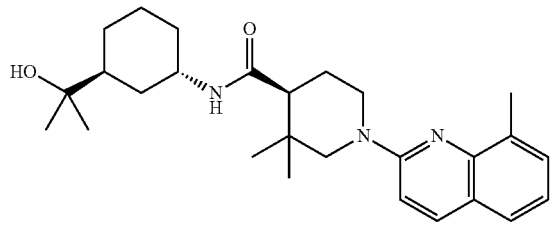 [SMILES: Cc1cccc2ccc(N3CC[C@H](C(=O)N[C@H]4CCC[C@H](C(C)(C)O)C4)C(C)(C)C3)nc12]

Add N,N-diisopropylethylamine (0.7 mL, 4 mmol) and HATU (0.31 g, 0.8 mmol) to a mixture of (−)-(4S)-3,3-dimethyl-1-(8-methyl-2-quinolyl)piperidine-4-carboxylic acid (0.2 g, 0.67 mmol), 2-[(1S,3S)-3-aminocyclohexyl]propan-2-ol hydrochloride (0.13 g, 0.67 mmol) and DMF (5 mL). Stir the resulting mixture at room temperature for 45 minutes. Subject the resulting reaction mixture to reverse phase flash chromatography on C18, eluting with a gradient of 5% to 80% ACN in water, to give the title compound (0.26 g, 88%). MS (m/z): 438 (M+H)$^+$.

Prepare the following Examples in Table 2 essentially by the procedure for Example 13 using the appropriate starting carboxylic acid in place of (−)-(4S)-3,3-dimethyl-1-(8-methyl-2-quinolyl)piperidine-4-carboxylic acid.

TABLE 2

| Ex. No. | Structure | Chemical Name | MS (m/z) (M + H) |
|---|---|---|---|
| 14 | 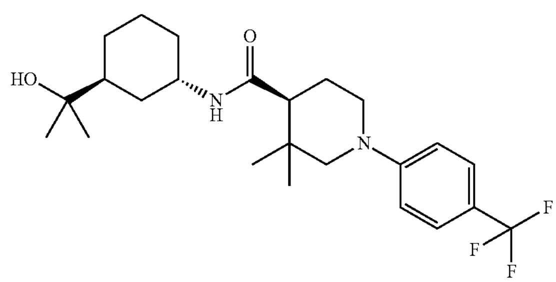 [SMILES: CC(C)(O)[C@H]1CCC[C@H](NC(=O)[C@H]2CCN(c3ccc(C(F)(F)F)cc3)CC2(C)C)C1] | (4S)-N-[(1S,3S)-3-(1-Hydroxy-1-methyl-ethyl)-cyclohexyl]-3,3-dimethyl-1-[4-(trifluoromethyl)phenyl]-piperidine-4-carboxamide | 441 |
| 15 | 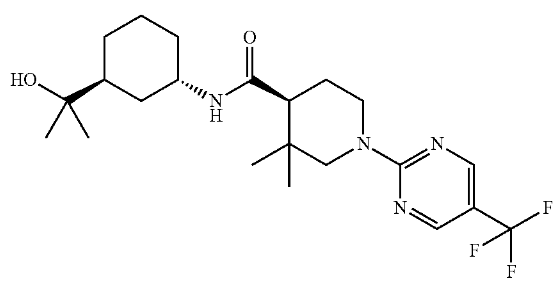 [SMILES: CC(C)(O)[C@H]1CCC[C@H](NC(=O)[C@H]2CCN(c3ncc(C(F)(F)F)cn3)CC2(C)C)C1] | (4S)-N-[(1S,3S)-3-(1-Hydroxy-1-methyl-ethyl)-cyclohexyl]-3,3-dimethyl-1-[5-(trifluoromethyl)-pyrimidin-2-yl]-piperidine-4-carboxamide | 442 |

Prepare the following Examples in Table 3 essentially by the procedure for Preparation 25 using the appropriate starting amine in place of methyl (±)-trans-5-aminotetrahydropyran-3-carboxylate and the appropriate starting carboxylic acid in place of (−)-(4S)-3,3-dimethyl-1-(8-methyl-2-quinolyl)piperidine-4-carboxylic acid.

TABLE 3

| Ex. No. | Structure | Chemical Name | MS (m/z) (M + H) | Purification Method |
|---|---|---|---|---|
| 16 | 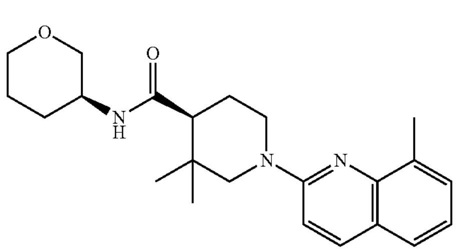 [SMILES: Cc1cccc2ccc(N3CC[C@H](C(=O)N[C@H]4CCCOC4)C(C)(C)C3)nc12] | (4S)-1-(8-Methyl-2-quinolyl)-3,3-dimethyl-N-[(3S)-tetrahydropyran-3-yl]-piperidine-4-carboxamide | 382 | A |

TABLE 3-continued

| Ex. No. | Structure | Chemical Name | MS (m/z) (M + H) | Purification Method |
|---|---|---|---|---|
| 17 | 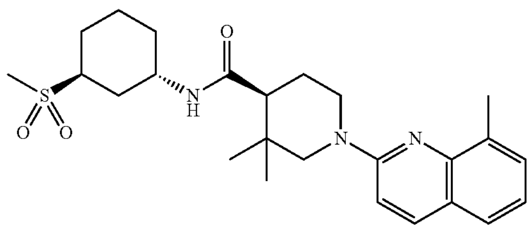 [SMILES: Cc1cccc2ccc(N3CC[C@H](C(=O)N[C@H]4CCC[C@H](S(C)(=O)=O)C4)C(C)(C)C3)nc12] | (4S)-3,3-Dimethyl-1-(8-methyl-2-quinolyl)-N-[(1S,3S)-3-methylsulfonylcyclohexyl]-piperidine-4-carboxamide | 458 | C |

Purification Methods: A=Crude product is purified by silica gel normal phase column chromatography, eluting with a gradient of EtOAc in hexanes. C=Crude product is purified by chiral column chromatography using chiral SFC (Chiralcel OD-H, 21×250 mm) using 25% EtOH (0.2% IPAm) in $CO_{2(scf)}$ as the mobile phase at a flow rate of 70 mL/min.

EXAMPLE 18

(S)-N-((3RS,5SR)-5-(Hydroxymethyl)tetrahydro-2H-pyran-3-yl)-3,3-dimethyl-1-(8-methylquinolin-2-yl)piperidine-4-carboxamide

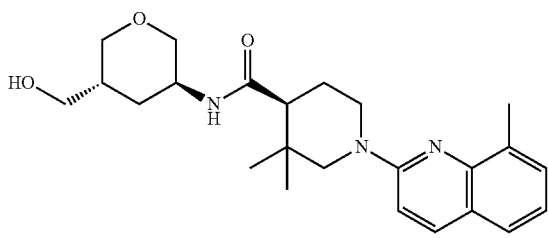 [SMILES: Cc1cccc2ccc(N3CC[C@H](C(=O)N[C@@H]4COC[C@@H](CO)C4)C(C)(C)C3)nc12]

Add a 5 N aqueous NaOH solution (0.5 mL) to a mixture of methyl (3RS,5RS)-5-((4S)-3,3-dimethyl-1-(8-methyl-2-quinolyl)piperidine-4-carbonyl]amino]tetrahydropyran-3-carboxylate (0.085 g, 0.19 mmol), MeOH (2 mL), and THF (2 mL). Stir the resulting mixture at room temperature for 1 hour. Add a 5 N aqueous HCl solution (0.5 mL) and concentrate. Dilute the crude mixture in THF (6 mL) and cool to 0° C. Add a 2 M solution of borane-THF complex in THF (0.15 mL, 0.3 mmol) drop-wise. Slowly warm the mixture to room temperature and stir at room temperature overnight. Add a saturated aqueous solution of sodium bicarbonate (10 mL) and extract the mixture with EtOAc (3×10 mL). Collect the organic extracts; wash with brine (10 mL); dry over MgSO$_4$; filter; collect the filtrate; and concentrate under reduced pressure. Subject the resulting crude material to flash chromatography on silica gel eluting with 100% EtOAc to give the title compound (0.046 g, 59% yield over 2 steps). MS (m/z): 411 (M+H)$^+$.

EXAMPLE 19

Methyl (1RS,3RS)-3-((S)-3,3-Dimethyl-1-(8-methyl-2-quinolyl)piperidine-4-carbonyl]amino]cyclohexanecarboxylic acid

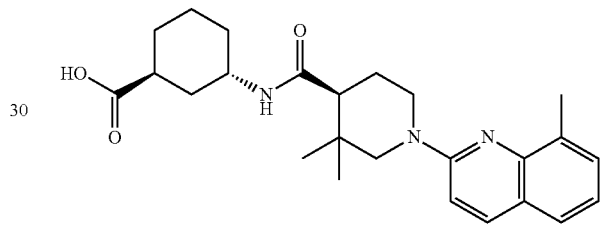

Add a 5 N aqueous NaOH solution (2.2 mL) to a mixture of methyl (±)-trans-[[(4S)-3,3-dimethyl-1-(8-methyl-2-quinolyl)piperidine-4-carbonyl]amino]cyclohexane-3-carboxylate (1.0 g, 2.2 mmol), MeOH (2 mL), and THF (8 mL). Stir the resulting mixture at room temperature overnight. Add a 5 N aqueous HCl solution (2.2 mL) to adjust the pH to 6.5. Extract with EtOAc (2×25 mL) and collect the organic extracts. Wash the organic extracts with brine (25 mL); dry over MgSO$_4$; filter; collect the filtrate; and concentrate under reduced pressure to give the title compound (0.935 g, 98%). MS (m/z): 424 (M+H)$^+$.

EXAMPLE 20

(S)-N-((1RS,3RS)-3-(Ethylcarbamoyl)cyclohexyl)-3,3-dimethyl-1-(8-methylquinolin-2-yl)piperidine-4-carboxamide

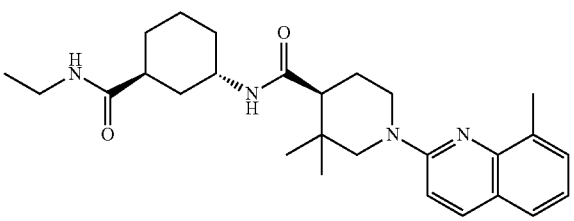 [SMILES: CCNC(=O)[C@H]1CCC[C@H](NC(=O)[C@H]2CCN(c3ccc4cccc(C)c4n3)CC2(C)C)C1]

Add triethylamine (0.7 mL, 5 mmol) to a mixture of (±)-trans-3-[[(4S)-3,3-dimethyl-1-(8-methyl-2-quinolyl)piperidine-4-carbonyl]amino]cyclohexanecarboxylic acid (0.9 g, 2 mmol), ethanamine (2 mL, 3 mmol), BOP (1.0 g, 3 mmol) and DMF (4 mL). Stir the resulting mixture at room temperature for 3 hours. Add a saturated aqueous solution of sodium bicarbonate (20 mL). Extract the resulting mixture with EtOAc (2×50 mL). Collect the organic extracts; wash with brine (3×25 mL); dry over $MgSO_4$; filter; collect the filtrate; and concentrate under reduced pressure. Subject the resulting material to reverse-phase flash chromatography on $C_{18}$ silica gel, eluting with a gradient of 20% to 80% acetonitrile (0.1% formic acid) in water (0.1% formic acid), to give the title compound (0.25 g, 30%). MS (m/z): 450 $(M+H)^+$.

Biological Assays

Human mPGES-1 Enzyme Inhibition Assay

Human mPGES-1 (Invitrogen™ (Cat#97002RG, clone ID 6374722)) is subcloned into pcDNA3.1 and transiently expressed in 293E cells. Microsomes are prepared from cell pellets based on published methods (Oullet et al., Purification and characterization of recombinant microsomal prostaglandin E synthase-1, Protein Expression and Purification, 26 pp 489-495 (2002); and Thoren et al., Human Microsomal Prostanglandin E Synthase-1, J. Biol Chem. 278(25) pp 22199-22209 (2003)). Briefly, pellets are brought up in homogenization buffer (15 mM Tris-HCl, pH 8.0; 0.25 M sucrose; 0.1 mM EDTA; 1 mM glutathione) and sonicated 5×30 seconds on ice. Homogenate is centrifuged at 5,000×g for 10 minutes at 4° C. The supernatant fraction is decanted and loaded into Beckman Quick-Seal® tubes and centrifuged at 150,000×g. for 90 minutes at 4° C. The supernatant fraction is discarded by decantation and the pellets are re-suspended in assay buffer (10 mM sodium phosphate, pH 7.0; 10% glycerol; 2.5 mM glutathione; Complete Protease Inhibitor Cocktail (Roche)). Protein concentration is determined using the Pierce Coomassie Plus™ reagent.

For the enzyme assay, the microsomes are diluted into assay buffer and 14 μL/well of the resulting solution is added to 384 well assay plates. Compound dilution plates (Nunc Cat#249944) are generated on a Tecan_MC384™ and 4 μL/well are added to the assay plates. Prostaglandin $H_2$ ($PGH_2$) is diluted into assay buffer immediately before use and 14 μL/well is added to the assay plates. Final concentrations are 6.55 μg/mL microsomes and 1.67 μM $PGH_2$. After a 1.5 minute incubation at room temperature, 5 μL/well of 1 mg/mL $SnCl_2$ in 0.5 N HCl is added to stop the reaction. Five μL of the stopped reaction are transferred to a 384 well plate containing 45 μL of 0.1% formic acid, and the plates are stored at 80° C. The plates are shipped to Agilent Technologies, formerly Biocius Lifesciences (Wakefield, Mass. 01880) for standard LC/MS analysis for $PGE_2$. The data are used to calculate the $IC_{50}$ (μM). The compounds of the Examples inhibit human mPGES-1 with an $IC_{50}$ μM value of less than 100 nM. The exemplified compound of Example 1 inhibits human mPGES-1 with an $IC_{50}$ μM value of 0.00193, ±0.00064, n=17. This result demonstrates that the exemplified compound of Example 1 is a potent inhibitor of the mPGES-1 enzyme in an isolated enzyme preparation.

Cell Based Assay for Measuring Eicosanoid Selectivity

Human epithelial lung carcinoma cell line A549 is obtained from ATCC (CCL-185) and maintained in Kaighn's F12 cell culture medium+10% fetal bovine serum (FBS) (plating medium) under standard 5% $CO_2$ humidified atmosphere at 37° C. The cells are passaged at 1:3 twice per week.

For the assays, cells are released from flasks by washing once with PBS, then once with Trypsin/EDTA. After 3-5 minutes at 37° C., the cells are suspended in plating medium and centrifuged at 2,000 rpm, 25° C., for 5 minutes. The supernatant is aspirated and the cell pellet is resuspended in F12K plating medium. The cell number is determined by counting an aliquot of cells which has been diluted in PBS and Trypan blue on a hemocytometer. Cells are plated at 40,000/well in 96 well Falcon plates 24 hours prior to treatment. Compounds are diluted in DMSO to 100× of the final concentration in Screen Mates tubes. The medium is removed from the cells and fresh medium (90 μL/well) is added to the cells. The compounds are added at 1 μL/well, n=2, to give seven concentrations each. Cells are pretreated with compounds for 30 minutes at 37° C., 5% $CO_2$. Prostaglandin $E_2$ production is induced by the addition of recombinant human interleukin (rhIL-1β) diluted in plating medium to 10× final. A 10 μL/well aliquot is added to give a final rhIL-1β concentration of 0.1 ng/mL. The treatment period is approximately 18 hours. Conditioned medium is removed to v-bottom polypropylene plates. The conditioned medium is assayed for levels of $PGE_2$ and prostaglandin $I_2$ ($PGI_2$) by specific enzyme immune-assay EIAs, according to the manufacturer's protocols (Cayman). Briefly, conditioned medium (1 μL) is added to each well of a 96 well plate coated with a capture antibody and containing EIA buffer (49 μL) supplied by the manufacturer. The tracer is diluted with the EIA buffer (50 μL). The detection antibody is diluted with the EIA buffer (50 μL). The plate is covered with adhesive sealing film and is incubated for 1 hour at room temperature on an orbital shaker at 100 rpm. The wash buffer is diluted into MILLIPORE purified water, and the plate is washed 5×350 μL/well, using a plate washer. The substrate (Ellman's reagent) is diluted with MILLIPORE purified water and then added to the plate at 200 μL/well. After approximately 90-120 minutes at room temperature on an orbital shaker at 100 rpm, the plates are read at A412 on a plate reader. A standard curve of $PGE_2$ is used to calibrate the unknowns. The exemplified compound of Example 1 inhibits $PGE_2$ formation with an $IC_{50}$ of 0.00471 μM±0.00301, n=2.

Human Whole Blood Assay

Blood is collected from normal volunteer donors into sodium heparin VACUTAINER tubes. Donors are selected, in part, on their confirmation that they have not taken NSAIDs, aspirin, Celebrex®, or glucocorticoids within two weeks of the donation. All tubes/donor are pooled into 250 mL Corning conical centrifuge tubes and 436.5 μL/well is distributed into deep well polypropylene plates. Compounds are diluted in DMSO to 100× final and 4.5 μL/well in duplicate or triplicate is added to give 7 point curves. The blood is pretreated with compounds at 37° C., 5% $CO_2$, in a humidified atmosphere, covered with a MicroClime Environmental Microplate lid, for 30 minutes after which 9 μL/well of a solution of 5 mg/mL of LPS (Sigma, serotype 0111:B4) in 1 mg/mL BSA/PBS is added to give a final LPS concentration of 100 μg/mL. The plates are incubated for 20-24 hours, at 37° C., 5% $CO_2$, in a humidified atmosphere. The plates are tightly sealed with the aluminum foil lids and are chilled on ice for approximately 1 hour. Then the plates are centrifuged at 1,800×g, 10 minutes, 4° C., in an Eppendorf 5810R centrifuge. Plasma is removed from the cell layer using the Rainin L200 with sterile filtered tips and transferred to v-bottom polypropylene plates. One hundred microliters is quantitatively transferred to Costar cluster tubes blocks and 400 μL/well of the MeOH stop reagent and internal standards, $d_4$-$PGE_2$, $d_4$-$PGF_{2\alpha}$, and $d_4$-$TXA_{2\beta}$ are added. Samples are vortexed for 5 minutes and are placed at −20° C. for at least one hour. Samples are centrifuged for 10 minutes at 4000 rpm in an Eppendorf 5810R.

Solid phase extraction is performed using Waters HLB 30 mg/bed 96 well plates on a vacuum manifold: Step 1, the matrix is washed with MeOH (1 mL), followed by 0.1% formic acid in water (1 mL); Step 2, 400 μL sample is applied along with 0.1% formic acid in water (900 μL) and allowed to bind for 5 minutes; Step 3, the matrix is washed with 0.1% formic acid in water (600 μL), followed by 80/20 water/MeOH (600 μL); Step 4, the products are eluted with 2-500 μL volumes of EtOAc; Step 5 the samples are dried under nitrogen and reconstituted in 75/25 water/acetonitrile with 0.1% formic acid (50 μL). The products are analyzed by LC/MS/MS. Example 1 inhibits The $PGE_2$ formation in this assay with an $IC_{50}$ of 0.00205±0.00082, n=11. This result supports that Example 1 inhibits $PGE_2$ synthesis in human whole blood.

What is claimed is:

1. A compound of Formula 1:

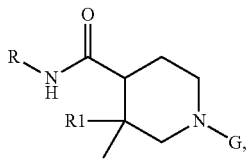

wherein:
R1 is H or —$CH_3$;
R is selected from:

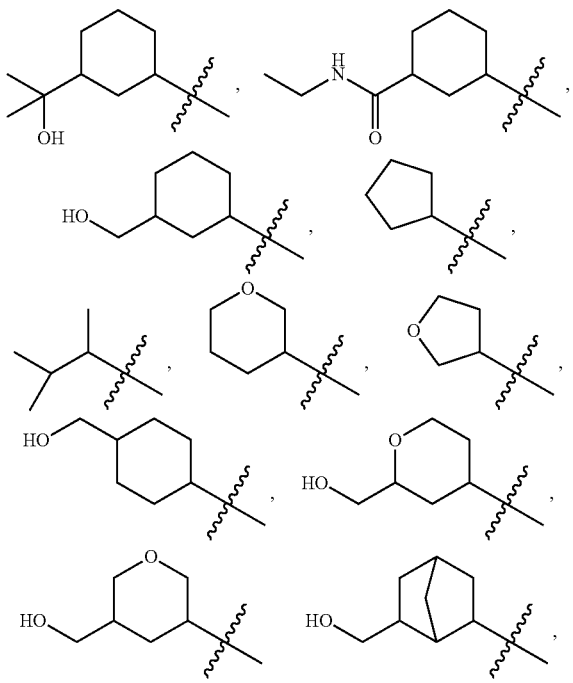

-continued

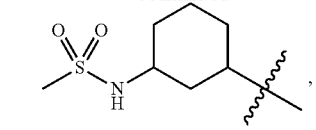

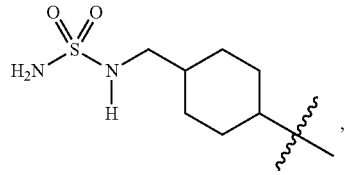

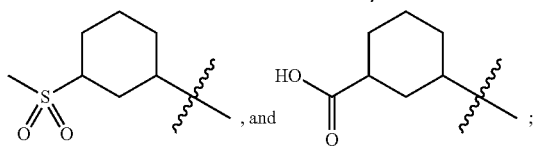

and
G is selected from:

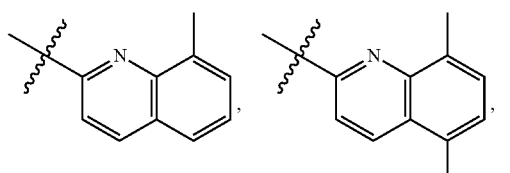

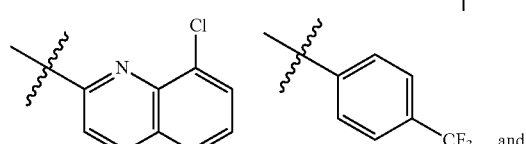

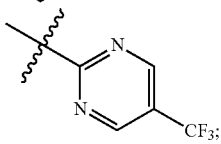

or a pharmaceutically acceptable salt thereof.

2. A compound according to Formula 2:

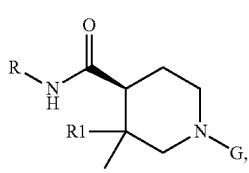

wherein:
R1 is H or —$CH_3$;
R is selected from:

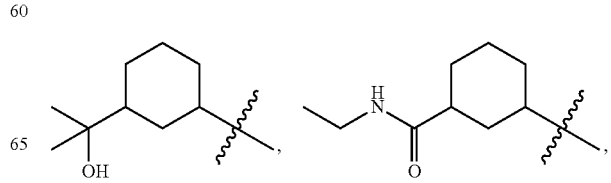

-continued
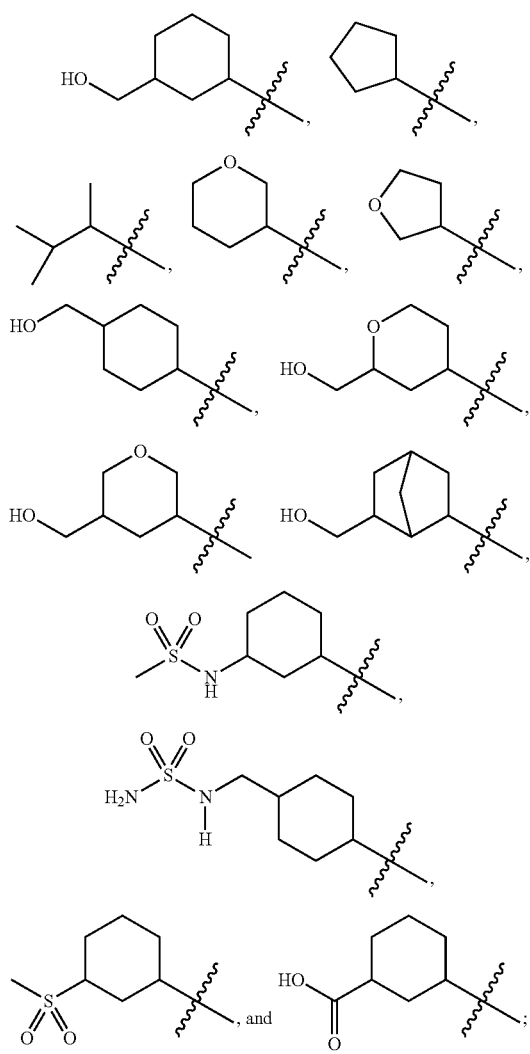
and
G is selected from:
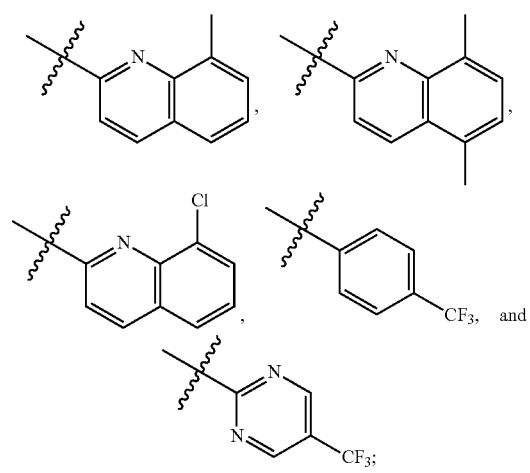
or a pharmaceutically acceptable salt thereof.
3. A compound according to claim 1:
wherein:
R1 is H or —CH$_3$;
R is selected from:
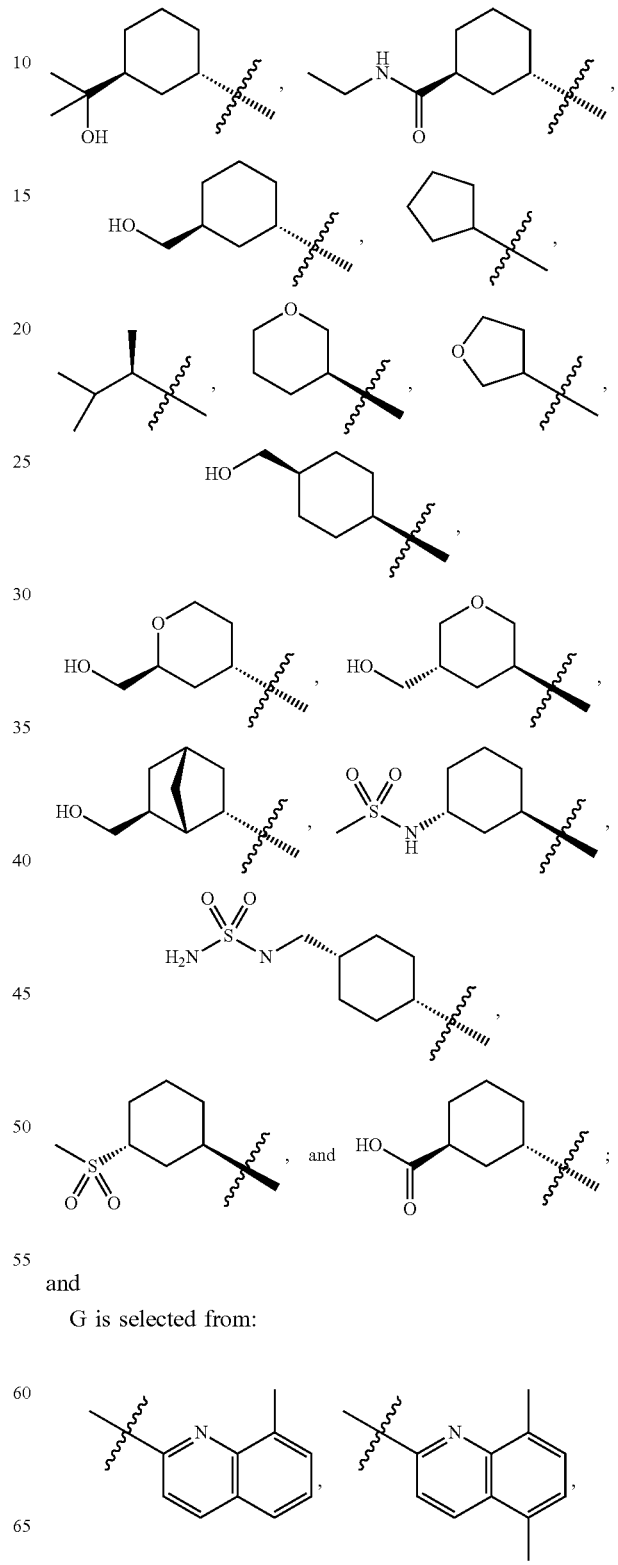
and
G is selected from:

-continued

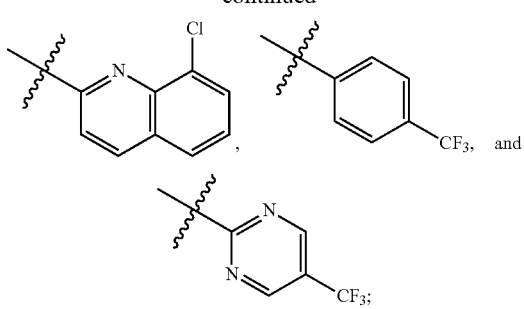

or a pharmaceutically acceptable salt thereof.

4. A compound according to claim 3, or a pharmaceutically acceptable salt thereof, wherein R is selected from:

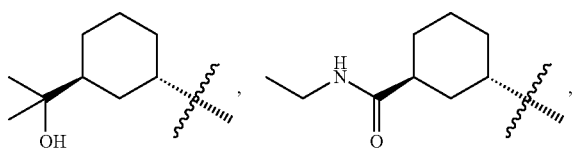

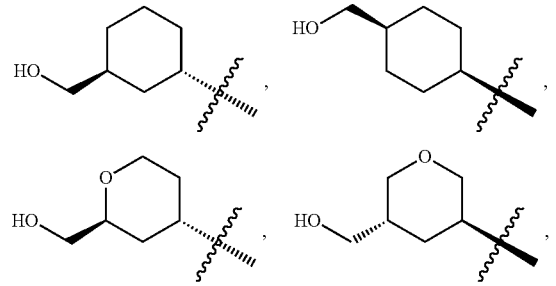

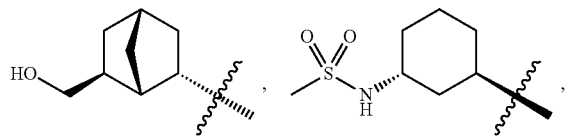

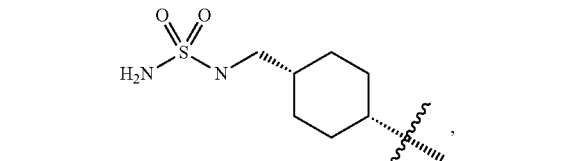

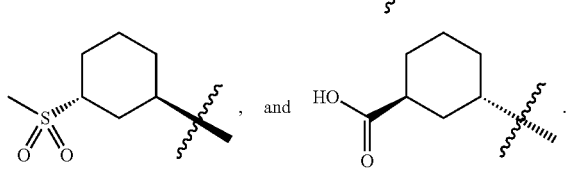

5. A compound according to claim 1, or a pharmaceutically acceptable salt thereof, wherein R is selected from:

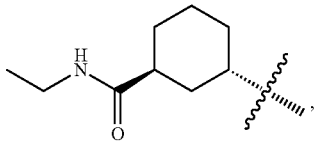

-continued

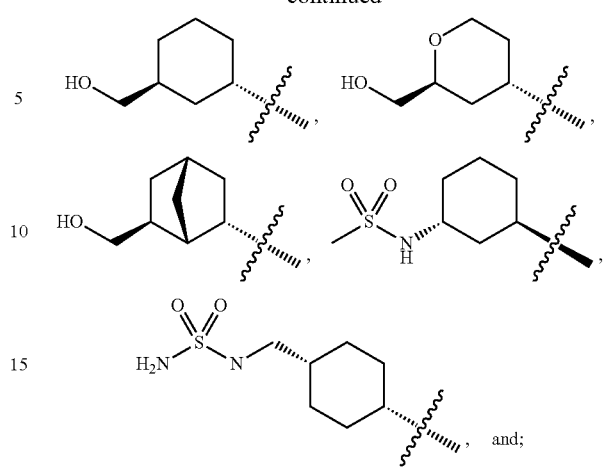

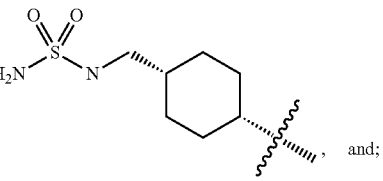

6. A compound according to claim 1, or a pharmaceutically acceptable salt thereof, wherein G is

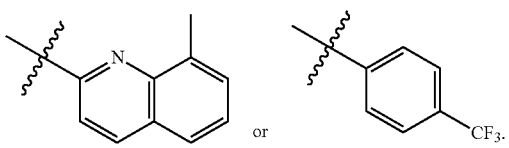 [SMILES: *c1ccc2cccc(C)c2n1 ; "or" ; *c1ccc(C(F)(F)F)cc1]

7. A compound according to claim 1, or a pharmaceutically acceptable salt thereof, wherein R1 is —CH$_3$.

8. A compound which is

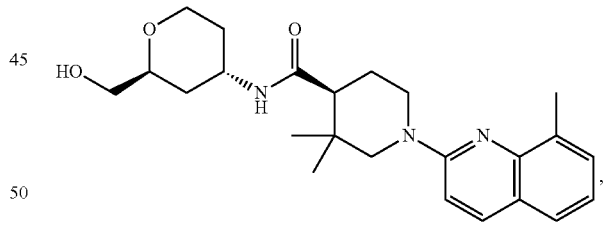

or a pharmaceutically acceptable salt thereof.

9. A compound according which is

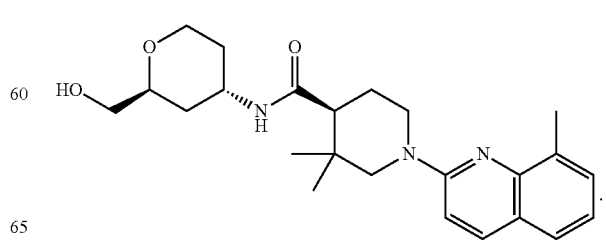

10. A compound according to claim 1, wherein the pharmaceutically acceptable salt is a hydrochloride salt.

11. A pharmaceutically acceptable composition comprising a compound according to claim 1, and at least one of a pharmaceutically acceptable carrier, diluent, or excipient.

12. A method of treating a patient in need of treatment for pain associated with arthritis or osteoarthritis, said method comprising administering to the patient an effective amount of a pharmaceutically acceptable composition according to claim 11.

13. A method of treating a patient in need of treatment for inflammation associated with arthritis or osteoarthritis, said method comprising administering to the patient an effective amount of a pharmaceutically acceptable composition according to claim 11.

14. A method of treating a patient in need of treatment for arthritis or osteoarthritis, said method comprising administering to the patient an effective amount of a compound according to claim 1.

15. A method of treating a patient in need of treatment for pain associated with arthritis, said method comprising administering to the patient an effective amount of a compound according to claim 1.

16. A method of treating a patient in need of treatment for pain associated with osteoarthritis, said method comprising administering to the patient an effective amount of a compound according to claim 1.

17. A method of treating a patient in need of treatment for inflammation associated with arthritis, said method comprising administering to the patient an effective amount of a compound according to claim 1.

18. A method of treating a patient in need of treatment for inflammation associated with osteoarthritis, said method comprising administering to the patient an effective amount of a compound according to claim 1.

19. A method of treating a patient in need of treatment for pain or inflammation associated with arthritis or osteoarthritis, said method comprising administering to the patient an effective amount of a pharmaceutically acceptable composition according to claim 11.

* * * * *

UNITED STATES PATENT AND TRADEMARK OFFICE
CERTIFICATE OF CORRECTION

PATENT NO. : 9,962,375 B2
APPLICATION NO. : 15/520462
DATED : May 8, 2018
INVENTOR(S) : Matthew Joseph Fisher et al.

Page 1 of 1

It is certified that error appears in the above-identified patent and that said Letters Patent is hereby corrected as shown below:

On the Title Page

Column 1 (Notice) (*) Line 3: Delete "days. days." and insert -- days. --, therefor.

Column 2 (Other Publications) Line 2: Delete "Biorganic" and insert -- Bioorganic --, therefor.

Signed and Sealed this
Eighteenth Day of June, 2019

Andrei Iancu
*Director of the United States Patent and Trademark Office*